United States Patent [19]

Shofner et al.

[11] Patent Number: 4,473,296
[45] Date of Patent: * Sep. 25, 1984

[54] SYSTEM AND METHOD AND APPARATUS FOR A CONTINUOUS AEROSOL MONITOR (CAM) USING ELECTRO-OPTICAL WEIGHING FOR GENERAL AEROSOLS

[75] Inventors: Frederick M. Shofner; Gerhard Kreikebaum; Arthur C. Miller, Jr., all of Knoxville, Tenn.

[73] Assignee: PPM, Inc., Knoxville, Tenn.

[*] Notice: The portion of the term of this patent subsequent to Feb. 3, 1998 has been disclaimed.

[21] Appl. No.: 428,867

[22] Filed: Sep. 30, 1982

Related U.S. Application Data

[63] Continuation of Ser. No. 34,746, Apr. 30, 1979, abandoned, which is a continuation-in-part of Ser. No. 902,510, May 3, 1978, Pat. No. 4,249,244.

[51] Int. Cl.$^3$ .................................. G01N 15/02
[52] U.S. Cl. ............................. 356/336; 356/338
[58] Field of Search ................ 356/336, 338; 250/574

[56] References Cited

U.S. PATENT DOCUMENTS

| | | | |
|---|---|---|---|
| 3,398,286 | 8/1968 | Ford et al. ............... | 356/338 X |
| 3,430,220 | 2/1969 | Deuth ....................... | 356/338 X |
| 3,563,661 | 2/1971 | Charlson et al. .......... | 356/339 |
| 3,713,743 | 1/1973 | Simms ....................... | 356/338 |
| 3,797,937 | 3/1974 | Shofner .................... | 356/336 |
| 3,810,697 | 5/1974 | Steinberg ................. | 356/338 |
| 3,869,208 | 3/1975 | Lorenz ...................... | 356/336 |
| 3,873,206 | 3/1975 | Wilcock ................... | 356/338 |

Primary Examiner—Davis L. Willis
Assistant Examiner—Matthew W. Koren
Attorney, Agent, or Firm—Kerkam, Stowell, Kondracki & Clarke

[57] ABSTRACT

A method and apparatus is disclosed for measuring the mass concentration of particulates entrained in a process or work area. One or more sensors are employed which electro-optically and continuously weigh the effluent extracted from the process area. The effluent is caused to enter a sample volume area either by convection or through a preseparator. The sampling volume is exposed to near infrared radiation of a light emitting diode (LED). An information signal indicative of small and large particulates entrained in the effluent is developed. The signal is converted and classified to signals corresponding to the presence of small or large particulates and further sub-classified as to size. The electro-optical "weighing" signals are operated on to produce a mass concentration read-out via an empirical algorithm exercised by a microprocessor in a centrally-located control/read-out unit which serves a multiple of remote sensors. The microprocessor also permits convenient automatic compensation of each sensor's electro-optical transfer function, i.e., baseline zero and span. Traceable calibration is also provided.

39 Claims, 23 Drawing Figures

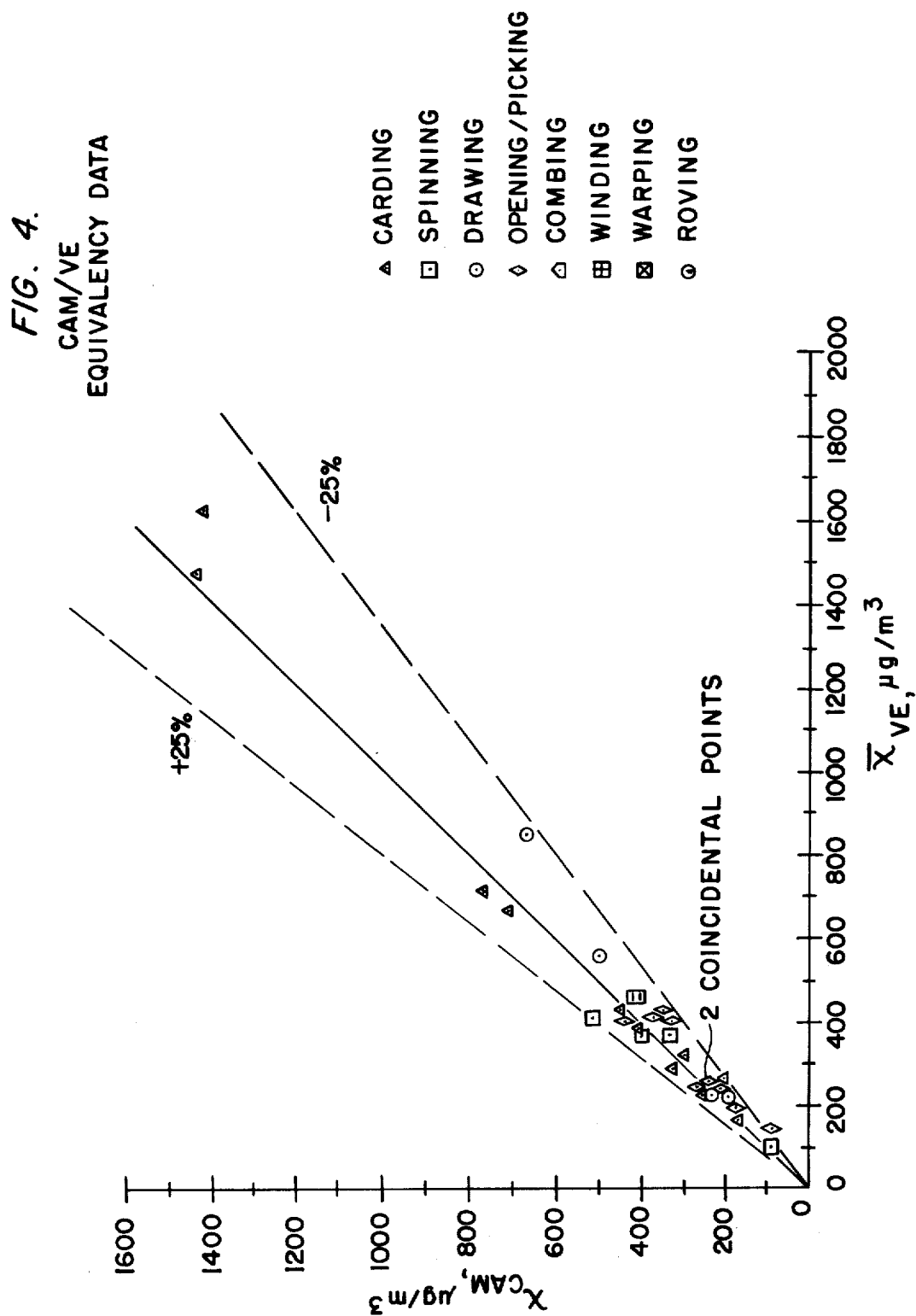

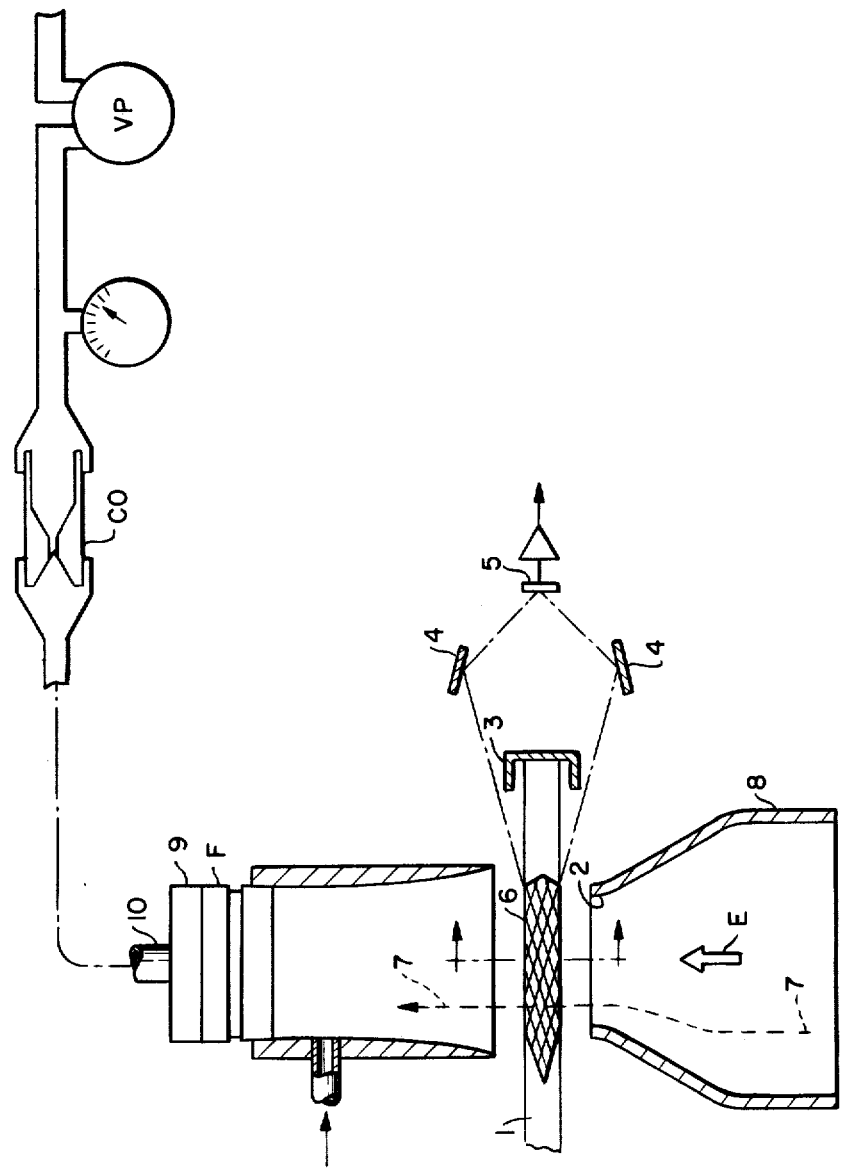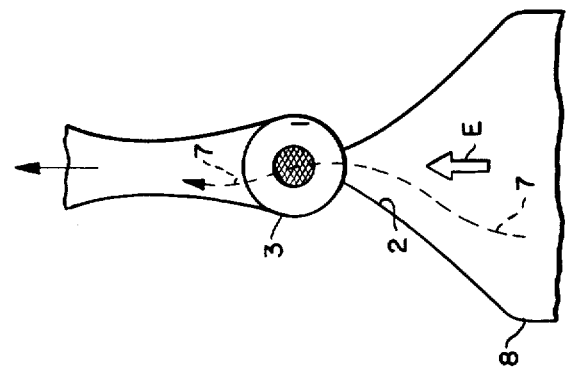
FIG. 5A.
FIG. 5B.

RESPONSE PER UNIT MASS OF ABSORBING PARTICLE DISTRIBUTIONS VERSUS PARTICLE DIAMETERS, FOR ABSORPTION INDICES $A_2 = 0, 0.1, 0.3, 1.96$ FOR FORWARD SCATTERING

RESPONSE PER UNIT MASS FOR NONABSORBING
PARTICLES AND LARGER FORWARD SCATTERING ANGLE

SYSTEM AND METHOD AND APPARATUS FOR A CONTINUOUS AEROSOL MONITOR (CAM) USING ELECTRO-OPTICAL WEIGHING FOR GENERAL AEROSOLS

CROSS REFERENCE TO RELATED APPLICATIONS

This application is a continuation of application Ser. No. 034,746, filed Apr. 30, 1979, now abandoned, which is a continuation-in-part of Ser. No. 902,510 now U.S. Pat. No. 4,249,244 of Frederick M. Shofner, Arthur C. Miller, Jr., and Gerhard Kreikebaum, filed May 3, 1978, for Electro-Optical System and Apparatus for Providing Automatically-Compensating Traceable Calibration and Zeroing for Light Scattering, the subject matter of which is hereby incorporated by reference.

BACKGROUND OF THE INVENTION

1. Field of the Invention

This invention relates generally to electro-optical measurement of the physical properties of materials whose particulate characteristics may be classified as being large and irregular in shape and with significant fractions of mass concentration associated with fibrous or flaky material having at least one dimension much larger than 3 $\mu$m. Cotton dust is a material which falls into this classification and, this invention relates particularly to the continuous in situ electro-optical weighing of cotton dust.

2. Description of the Prior Art

Reference may be made to U.S. Pat. Nos. 3,797,937; 4,017,186; both of which relate to electro-optical measurement techniques. U.S. Pat. No. 3,797,937 describes a system for making particle measurements by forward scattering of laser light. U.S. Pat. No. 4,017,186 describes an electrical-optical method and system for in situ measurements of particulate mass density using back scattering techniques. The latter patent is concerned only with measurements of particulates which fall in the range of 0.3$\lambda$ to 3$\lambda$.

Overwhelming scientific evidence supports the finding that cotton dust produces adverse health effects among cotton workers. The disorders range from an acute reaction manifested by a depression of pulmonary function indicators, or by subjective symptoms such as chest-tightness, shortness of breath, or cough, to a stage characteristic of chronic obstructive pulmonary disease which is often disabling. The chronic stages of cotton dust induced respiratory disease are, as a clinical entity, similar to chronic bronchitis or emphysema. While gaps exist in the understanding of the etiology of respiratory disease caused by cotton dust and their progression from acute to chronic stages, evidence supports the fundamental connection between cotton dust and various respiratory disorders in both the textile and the non-textile industries.

Because of the recognized health dangers of cotton dust, the Department of Labor through the Occupational Safety and Health Administration (OSHA) has adopted occupational safety and health standards related to occupational exposure to dust. Monitoring of exposure levels and dust sampling is of increasing importance to the cotton industry.

Cotton dust ranges in size from particles large enough to be visible to the naked eye to those which are submicron in size. The shape of the particles is also irregular. Therefore, particle size is equated with the "aerodynamic equivalent diameter," i.e. the size of a unit density sphere having the same settling velocity as the particle in question, of whatever size, shape or density. Most investigators believe that a better correlation exists between respirable dust and health effects, since total dust measurements include a significant fraction of particles which are too large to be deposited in the respiratory tract, but the question has not been settled conclusively. Early studies have involved the use of the vertical elutriator for measuring employee exposure to cotton dust. These instruments have a theoretical cutoff of 15 microns. While this method collects somewhat more than the respirable fraction, including particles larger than approximately 15 microns in size, exposure data derived from the use of the vertical elutriator is primary from smaller dust particulates; little information is available on the layer particles normally considered too large to be deposited deep in the respiratory tract. Nevertheless, the vertical elutriator has been accepted in the industry as a valuable monitoring tool.

The vertical elutriator operates on the principle that particles with settling velocities less than the velocity of an air stream will be carried upward by a stream of air in a cylinder. The flow rate of 7.4 liters/minute is required to achieve cut off size at 15 $\mu$m. The larger particles, with settling velocities greater than that of the vertical air stream, will settle out during their course of upward motion and will not be measured, whereas the smaller particles reach the top and are collected on a filter.

The acceptance of the vertical elutriator in the industry, both for research and periodic monitoring purposes, does not diminish its attendant disadvantages. The vertical elutriator, including pump, is approximately three feet in height, six inches in diameter and weights approximately 15 lbs.; therefore, its use at its current stage of development generally requires fixed sampling sites. Further the particles in its effluent which are collected on the filter must thereafter be measured by gravimetric techniques, and as hereinbefore noted, the effluent tends to include larger particles. although The presence of lint type particulates on filters diminishes the validity of such measurements for medical purposes.

Determining exposure to cotton dust in a large plant may require many samples. Since several hours are required for each sample, it is obvious that to complete the sampling, several days may be required and a number of units must be used simultaneously. Set up and labor costs are thus high. Other problems in using the vertical elutriator are: the necessity of relatively regular maintenance for its motors; the time consumed in the process of pre- and post-sample weighing of filters; the difficulty of calibration and maintaining calibrated flow rates; and, because of their size, the susceptiblity of samplers to damage during transportation.

Other sampling devices have been utilized for collecting respirable cotton dust. A GCA dust monitor with miniature vertical elutriator attachment utilizes the principle of a radioactive source to determine the amount of impacted dust. At higher dust levels (generally about 700 $\mu$g/m$^3$), its correlation with the vertical elutriator results is erratic.

The use of the horizontal elutriator and Hexhlet has been tried by some investigators as has a cyclone apparatus attached to a high volume sampler; however, this apparatus is even more bulky, expensive, and complicated than the vertical elutriator.

While the vertical elutriator (VE) has evolved as the primary sampling device in the textile industry and has served the textile industry well, it is generally recognized that alternative measurement methods could, desirably, reduce the cost of cotton dust measurements and, hopefully, increase their precision and accuracy. Many have commented on VE performance and data interpretation. Some have suggested that improved means can and ought to be used for the measurement of cotton dust. Such comments and question arise primarily because the actual VE penetration efficiency is not known.

Penetration efficiency $F(d_i)$ is defined as $$F(\overline{d_i}) \triangleq \text{mass fraction of particle size class } (\overline{d_i}, \Delta d_i), \quad \text{(A-1)}$$
classified and collected from workplace air sample $$= \frac{\text{mass concentration of collected particles in } (\overline{d_i}, \Delta d)}{\text{mass concentration of workplace particles in } (\overline{d_i}, \Delta d_i)}$$

$$= \frac{\Delta x(\overline{d_i}, \Delta d_i) - \text{collected}}{\Delta x(\overline{d_i}, \Delta d_i) - \text{workplace}}$$

The interval $(\overline{d_i}, \Delta d_i)$ describes the range of particles in the ith class and may be taken as $\overline{d_i} - d_i/2 < d < \overline{d_i} + \Delta d_i/2$. $\Delta \chi$ is the mass concentration (i.e. mass/unit volume of sampled air) and usually has dimensions of $\mu g/m^3$. The total mass concentration is $\chi = \Sigma \Delta \chi_i$. $\chi$ can obviously be computed for the collected sample or for the total workplace or environment air, provided the respective $\Delta \chi_i$'s are known from sizing or classifying measurements, such as cascade impactors or optical analyzers.

Total $\chi$'s are also directly measureable. Historically, the simple, integrating measurements are performed first, before more difficult classifying measurements are made. The VE method yields $\chi_{VE}$. An open-faced filter or total dust sample yields $\chi_T$ for the workplace. Particle size information can be generated by microscopic, optical or electron analysis of the filters.

The ideal and commonly understood-VE penetration efficiency is, by definition, $$F_{ideal} = \begin{cases} 1, \overline{d} < 15 \ \mu m \\ 0, \overline{d} > 15 \ \mu m, \end{cases} \quad (1)$$

However, it is known that particles having aerodynamic equivalent diameters larger than 15 $\mu$m can be and are collected. This is in addition to fibrous ("lint") or flakey particles frequently observed on the filters and commonly accepted as normal by cotton dust measurement practitioners. Lint particles can have lengths of several hundred micrometers.

Thus, the actual VE penetration efficiency F actual departs significantly from F ideal, especially for large particles. Despite the recognized failings of VE measurements, cotton dust sampling has followed the historical trend. Dust measurements with the VE and total dust sampler, which do not give mass fractions, were performed first and are far more common. Thus, the VE constitutes the basis for the cotton dust standard. Since size-resolved or size-classified measurements (i.e., $\Delta \chi_i$) are more difficult and expensive, they have in the past been generally only performed by specialists for research purposes, and are sparsely published. This partially explains why the actual penetration efficiency for the VE is poorly known; sufficient $\Omega \chi_i$ data are not readily available to permit unequivocal specification of F actual.

SUMMARY OF THE INVENTION

The present invention provides an alternative measuring technique to the historically accepted vertical elutriator. Its operation may be simply described as in situ electro-optical weighing of particulates entrained in sample effluent extracted from ambient air. The electro-optical detection means enables infrequent large particles to be sensed with high signal to noise ratio. The total response is corrected for inherent underweighing errors when applied to mass concentration measurements. The approximate size distribution for the large particles is also given.

While the invention is applicable to mass concentration in a variety of environments, it is particularly applicable to large cotton mills wehre a need exists for classifying particulates and deriving meaningful statistical data on the presence of particulates of various sizes. In a large exposure area, multiple sensors are connected to a centrally located Control/Read-Out (CRO) unit through an umbilical containing air and electrical connections with quick disconnect connectors to permit quick disconnection of the lines from their fittings. Thus, a sensor may be permanent for continuous monitoring or moving to any one of several locations along its respective umbilical for periodical tests. Alternately, the sensor may be miniaturized and housed conveniently in a casing suitably attached to a worker to serve as a personal monitor.

Effluent is exposed to radiation from an electro-optical transducer either by convection currents or a preseparator combined with the effluent monitor. Sample air is drawn through a sample or weighing volume defined by the radiation acceptance geometry of the electro-optical transducer. Periodically, air flow may be reversed to purge internal ports of the transducer and establish a zero baseline reference with clean air. Calibration of the system is automatically checked during this interval. In the electro-optical transducer or sensor, a light beam is generated by beam-forming optics which collect and collimate radiation from a light emitting diode (LED). The LED is in turn driven by a LED driver. The LED beam is turned on and off in a rectangular wave fashion at a periodic rate, being controlled by an internal clock timer through an electronic switch. Particles entrained in the effluent entertain scattering in the weighing volume defined by the joint intersection of the LED beam and the radiation acceptance optics of the collection optical system. The collected radiation is converted into a voltage signal containing the particle information and the signal is processed to a microprocessor. The microprocessor receives signal information in the form of "counts", which is optimal for digital processing techniques. The microprocessor software determines which of the multiple sensors will receive a gating pulse and deliver its signal voltage for "number-crunching".

After signal acquisition and conversion to mass concentration through explicit and empirical algorithms, the microprocessor presents its data in one of several forms, including but not limited to:

(1) a digital print-out of time-weighted averages of mass concentration for each of the sensors;

(2) a LED display of instantaneous dust concentration at any one of the sensors; and (3) Analog chart record.

Dust concentration data from each of multiple sensors are quickly computed in the microprocessor based control read/out unit.

DEFINITION OF ELECTRO-OPTICAL "WEIGHING"

Simplistically, the operation of the CAM Sensor may be viewed as an electro-optical transducer which weighs the effluent of the VE preseparator. Particles within the weighing or scattering volume scatter radiation into the collection optics and thence to the detector. This signal is electronically converted by the microprocessor in the control/read-out unit into the weight of the particles. The final output is proportional to the mass of the particles per unit volume of space, but this is precisely, by definition, the mass concentration of the dust or aerosol.

It is instructive and interesting to pursue this electro-optical weighing viewpoint with a simple example. Suppose that the weighing volume is one cubic centimeter and that there is, in the average, one spherical particle having d=5 μm and density=1.5 gm/cm³ (approximately that of cotton dust) within this sampling volume. This corresponds to an average mass concentration of $$\chi = \frac{mass}{volume} = \frac{\rho\pi/6 d^3}{vol} = 98 \times 10^{-12} g/cm^3 = 98 \ \mu g/m^3 \quad (2)$$

This particle size and concentration are fairly representative of actual dust levels. This value of $\chi$ is about half the permissible exposure level (PEL) of the recently enacted cotton dust standard. The standard requires that $\chi \leq 200 \ \mu g/m^3$ for most yarn manufacturing processes.

The subject CAM sensitivity is of the order of 10 μg/m³. This means that short-term changes in mass concentration of 10 μg/m³ may be reliably sensed. A 2.34 μm spherical particle having $\rho = 1.5$ and average concentration of one/cm³ contributes 10 μg/m³ to the average mass concentration. Therefore, its presence or absence in the weighing volume may be sensed. But the 2.34 μm particle weights $10 \times 10^{-12}$ g = 10 μμg = 10 pg (p="pico"=$10^{-12}$) And the measurement is a few tens of milliseconds.

ADVANTAGES AND OBJECTIVES OF THE INVENTION

This weighing sensitivity and measurement time of the subject CAM may be compared to conventional vertical elutriator, gravimetric methodology. The weighing sensitivity (or precision) of a microbalance is of the order of one microgram. The balancing time for a skilled operator is of the order of a few seconds. Clearly, the electro-optical method of the present invention is many orders of magnitude more sensitive and faster than the comparable weighing mechanism of the gravimetric method.

Weighing accuracy and precision of the CAM electro-optical method of the present invention depend on maintenance or knowledge of (1) electro-optical transfer function and (2) particle characteristics. Both sensitivity and zero baseline (i.e. electro-optical transfer function) are maintained automatically. Sensitivity is known from the traceable calibration; zero is determined with dust-free air.

Knowledge required of particle characteristics is very general. That is, CAM sensors calibrated for cotton dust will yield accurate readings of mass concentration for a fairly wide, practical range of size and shape distributions and composition. Vastly different particle characteristics may necessitate minor adjustments in gain; such large differences in particle characteristics are vertically-elutriated cotton dust versus micron-sized oil mist or acid mist. Indeed, even in earlier instruments, responses, to cotton dust and air pollution were quite similar. For the CAM system, variations in particle charactaeristics between, say, carding and spinning, although quite real, have minor influence on CAM response, as shown in the next section.

One essentially independent parameter set for electro-optical weighing is fluid dynamic properties of the sample in which the particles are entrained. Electro-optical weighing is very insensitive to flow rate, pressure, temperature or gas composition of the sample fluid. (Of course, if these parameters affect the particles transported into the weighing volume, the response is to their actual weight.) Sample flow rate in the CAM can be established with critical orifices and is monitored by the control/readout unit.

For comparison, good mass concentration measurement accuracy and precision of the VE gravimetric method require maintenance or knowledge of (1) microbalance accuracy and precision
(2) critical orifice calibration;
(3) air temperature;
(4) air pressure; and
(5) humidity.

Items (1) and (2) are tedious and labor-intensive. Although T, p, and RH data are relatively easy to acquire, the correct formulas are not trivial to implement. The electro-optical system of the present invention is worthy of mass application in high concentration dust environments, and is able to make reliable, accurate and cost effective measurements.

Other objectives and advantages of the present invention is to provide traceable calibration, automatically-compensating and self-diagnostic signal conditioning, mass concentration sensitivity of order of 1 μg/m³, and in situ, continuous measurement of a wide variety of particulate characteristics, including size, shape and composition.

In addition, the refinements and specializations of the present invention have the following exemplary, but not limiting, objectives and advantages:

(1) Accurate, precise, and cost-effective in situ measurement of large, irregularly-shaped aerosols of varying composition such as cotton, coal, grain, wood, glass, silica, road, and rock dusts, and the like, through "electro-optical weighing";

(2) Compensation of the scattering signals for large particles such that their mass concentration contributions are determined;

(3) Electro-optically weighing the effluent of various "prefilters" or "preseparators", such as the vertical elutriators, cyclones, impactors, precipitators, etc.;

(4) Electro-optical simulation of various preseparator penetration efficiency responses by means of explicit or empirical algorithms;

(5) Measuring the dry or desiccated weight of the aerosols;

(6) Multi-sensor operation, with each sensor simultaneously serviced by a centralized control/readout unit utilizing a microprocessor for "number-crunching";

(7) Long-term (hours or days) measurements with provision of a final data product in the format of a printed, time-weighted average suitable for engineering or administrative use, such as OSHA compliance;

(8) Short-term (seconds or minutes) measurements, suitable for trouble-shooting dust control equipment thorugh "cause and effect" analysis.

(9) Determining mass fractions of various size classes of particles.

(10) Determining surface area of particles per unit volume of gas or air.

The present invention meets the above-stated objectives by application of the basic principles of scattering of electro-magnetic radiation, hereinafter called light or radiation for simplicity.

Traceable, automatically-compensating calibration is implemented in the present invention by periodically and rotationally inserting calibration element(s) into the LED beam, essentially according to the teachings of the aforenoted application Ser. No. 902,510 now patent 4,249,244. The present invention offers simplifying refinements applicable to certain nonhostile and low-concentration aerosol concentrations such as found in cotton, wood, coal and other workplace environments, wherein it is desirable to monitor worker or equipment exposure, or in process conditions by conveniently carried portable personal monitors which avoid the use of pumps and preparators, relying on convection currents generated by worker movement.

Zeroing on the electro-optical system is accomplished by flowing clean air through the sample or weighing volume.

Both calibration and zero are implemented for the entire electro-optical train, with all components "live".

BRIEF DESCRIPTION OF THE DRAWINGS AND PREFERRED EMBODIMENT

FIG. 1 shows a representative CAM sensor and bracket installation I. The sensor S is mounted in the permanently-installed terminal bracket TB and a vertical elutriator 8 is used as a preseparator. The electrical and airflow schematic insert of FIG. 1 illustrates how multiple locations along an umbilical U consisting of an air line $AL_2$ and electrical cable EC may be employed. That is, electrically, plugging the connector on the pigtail into the terminal box TB "tees" the sensor into the electrical cable; and, similarly, inserting the quick-connect plugs P into their respective sockets "tees" them into the air line.

A single air line $AL_2$ is used to both draw sample into the elutriator 8 and past the CAM sensor weighing volume and to supply, with reversed flow, clean air for zeroing of the instrument. The check valves $V_1, V_2$ assure proper flow direction. The line filter F precludes contamination of the air line. Other means for drawing the sample and supplying zero and purge air could be used. In another embodiment, a small pump located at the sensor installation could drive the flows in either direction.

An important and practical alternative is to drive the sample flow convectively. This is done by heating the internal surface of the elutriator, so that not only is the sample flow driven, but also the particles are desiccated during their several-second time of flight from inlet to electro-optical measurement.

FIG. 2 shows schematically a typical CAM system multiple sensor installation for a cotton mill with a permanently-installed umbilical network, each of which connects one or more sensors through one or more terminal lines. This indicates how a single sensor may be located at any number of points along its respective umbilical line. This permits more effective use of the equipment. The figure also shows the centralized nature of the control/readout unit. Not only are the mass concentration data centrally processed and made available to the user, but also the sample and zero purge flow performance may be centrally determined.

The inset of FIG. 2 shows an exemplary print-out, which is a final data product of time-weighted averages of mass concentration for the respective sensors, at their known locations, and for the preselected averaging time.

Also shown are instantaneous displays via light emitting diodes in the control/readout unit and an auxiliary chart recorder. Both are useful for short-term diagnostics of dust control system performance and problems. Note, finally that the data format of the control/readout unit, being a microprocessor-based unit, is inherently suitable for interface with other computing equipment.

FIG. 3 shows an exemplary chart record obtained from one sensor location. In this example, an analog chart indication of the dust concentration in a picker room is shown. Note the "blow down spike" due to cleaning the equipment with compressed air. Also note, for later reference, the "lint spikes". This particular example is chosen to prove the existence of large fibrous material as determined by the CAM sensor method.

FIG. 4 shows a correlation plot of CAM readings of dust concentration versus the average of vertical elutriator readings in contemporaneous or simultaneous side-by-side tests. These data establish the equivalency of the CAM method to the vertical elutriator, the reference method for OSHA dust level compliance.

FIG. 5 is a diagrammatic view of the flow cell in the CAM sensor, a central component of the method. Only the sampling volume and flow arrangements are shown. Not shown is the calibration/zero element function or location. This is discussed separately later in this application, but the major concepts have already been disclosed in the parent application Ser. No. 902,510 now U.S. Pat. No. 4,249,244.

DESCRIPTION OF THE PREFERRED EMBODIMENTS

Figure 1:
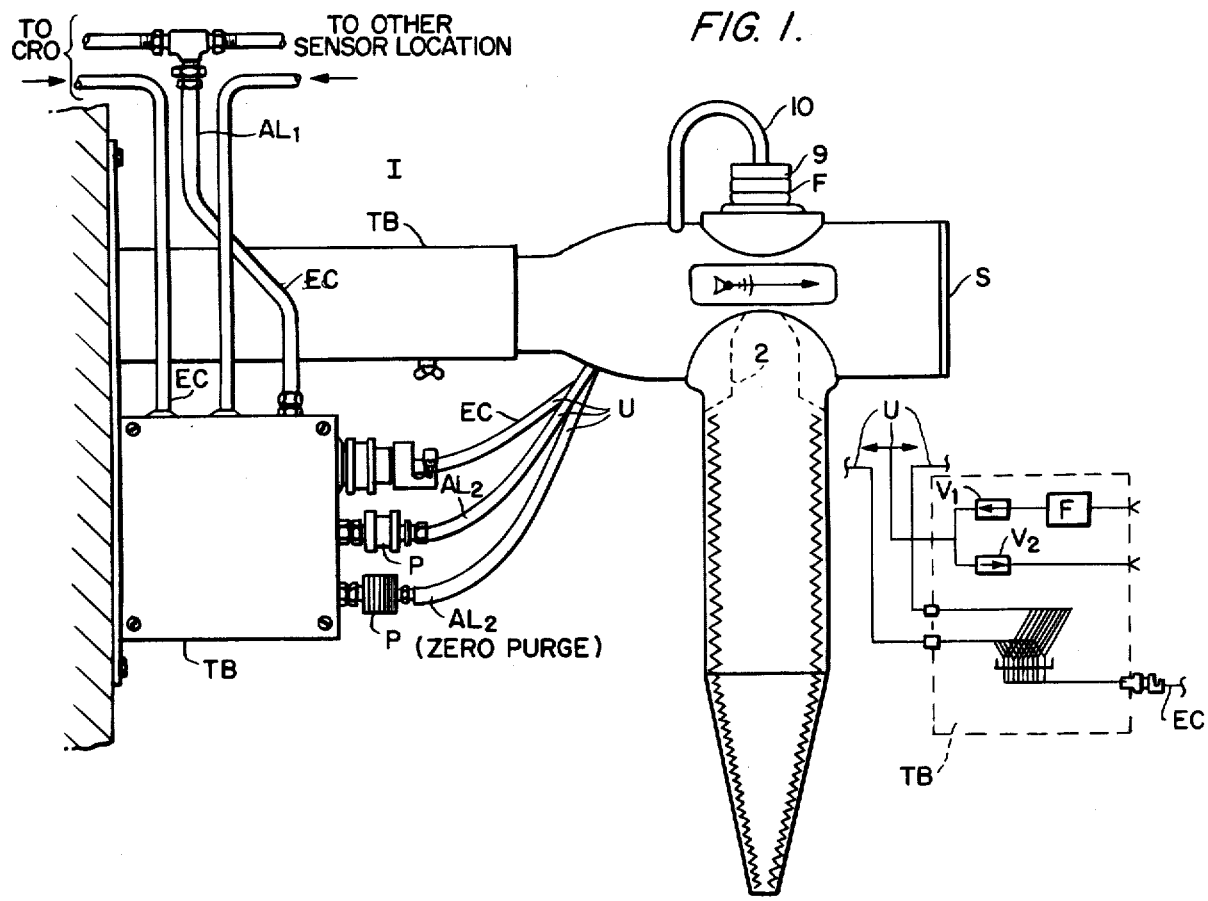

Whereas FIG. 1 shows the exterior features of a stationery embodiment of the invention adapted for cotton dust measurement, FIG. 5 is a diagrammatic of the essential internal components of the invention for electro-optical weighing. The traceable calibration provisions are not shown for clarity and are discussed later.

An essentially collimated beam of radiation of wavelength $\lambda$ is formed into the LED beam 1. This approximately cylindrical beam of diameter $\delta$ is made incident upon the effluent E of an aerodynamically converging slot 2 and entertains light scattering with particles entrained in the fluid effluent. The beam, which is typically attenuated by a very small amount, is finally incident into a blocking filter or "beam dump" 3.

The cylindrical beam 1, in combination with the collection optical system consisting of a conical mirror 4 and an effective aperture on the detector 5, form a weighing or scattering volume 6 shown cross-hatched in FIG. 5a. The dimensions of this weighing volume are chosen in view of the anticipated application for aerosol measurement and more specifically according to the mass concentration and particle size distribution of the particles being measured, as explained below. These interrelated design choices are fundamental to the invention.

As shown in the embodiment of FIG. 5*a*, the particles passing through the converging slot 2, with typical particle trajectories 7, represent those particles which have been prefiltered or preseparated by, in this case, a vertical elutriator 8, a full exterior view of which is shown in FIG. 2.

The vertical elutriator accomplishes prefiltering (or preseparation) by having a mean upward velocity such that particles larger than a chosen aerodynamic diameter are unable to ascend the flow, but rather, after being drawn into the inlet fall to the sides of the elutriator. However, other forms of preseparators, such as, for example, a cyclone or impactor, may be used to draw a representative sample of air into the area of the sample volume 6. Alternatively, the air may be drawn into or transported across the weighing volume by convection currents.

In the VE, only particles having equivalent aerodynamic diameters smaller than the design size will ascend the flow, pass through the converging slot, and be weighed. For example, for cotton dust measurement, the mean updraft velocity in the elutriator is approximately 0.7 cm per second. This flow will leviate a spherical particle of unit density with 15 m diameter. That is, such a particle has an equilibrium of Stokes settling velocity of approximately 0.7 cm per second.

It should be noted that the aerodynamic equivalent of non-spherical particles is sometimes difficult to describe. For the case of fibrous material, if the aspect ratio, ratio of lenglth to diameter, exceeds approximately 3, the aerodynamic equivalent diameter of the fiber then approaches its fiber diameter and becomes weakly dependent on length. This is why very long particles, hundreds and sometimes thousands of micrometers in length are frequently observed in the vertical elutriator effluent. They are sometimes referred to as as lint and frequently referred to as undesirable to the measurement for, presumably, they are not injurious to health. Nevertheless, their contributions to mass concentration must be measured and a major part of the present invention has been conceptualization and development of procedures to accurately and precisely accomplish this difficult task by electro-optical means. Since the updraft velocity in the elutriator is relatively low, it may be driven with a variety of means. Commonly, the VE effluent is drawn in through a filter cassette 9, and into a sample line 10, and to a critical orifice CO and vacuum pump VP combination, well known in the art for precise flow determination. For gravimetric measurements with the vertical elutriator, a membrane filter 7, commonly having a pore size of 5 $\mu$m, is placed in the filter cassette. Since the difference of the filter weight before and after exposure represents the mass of particulates captured from the flow, and since the flow rate and the exposure time are accurately known, it follows that the mass per unit volume of sampled air is determined. In some cases, corrections for air temperature, pressure and humidity of the sampled particles are made. This latter correction is commonly made by desiccating the filter before and after exposure to insure that moisture contributions to the particulate weights are not made.

An advantageous alternative for driving the flow and simultaneously desiccating the particles (e.g., removing moisture from them) is to heat the interior walls of the vertical elutriator so that the flow is driven convectively. As shown in FIG. 1, internal resistance wires may be provided for this purpose. Other heating means and methods may also be used.

The penetration time between inlet and measurement is, theoretically, 46 seconds, for a half-scale vertical elutriator with cylindrical column length of 8 inches and conical divergent cone length of 6 inches. In practice, the penetration is shorter but still, in average, about half the theoretical value. During this time, the moisture is driven from the particles into the gaseous phase. Thus, those particles which arrive through the converging slot are weighed "dry".

We now turn to the means by which mass concentration ($\chi$) readings are derived from forward scattering signals. In overview, we first show how under certain circumstances the scattering signal is proportional to $\chi$; we show the severity of underweighing errors for large particles and show how to compensate for them. Finally, we show how to incorporate traceable automatically-compensating calibration and zero means into an embodiment for workplace or process particulate monitoring.

Light-Scattering Basis of CAM Measurement

The amount of light scattered by a spherical particle of diameter d and complex index of refraction $m = m_1 - jm_2$, where $m_1$ is the ordinary index of refraction and $m_2$ is the absorbing index, is well known and is commonly referred to as Mie scattering. Gustav Mie published the first rigorous solution to this boundary value problem of electro-magnetic field theory in 1908. It can be shown from the Mie theory that the asymptotic behavior for the light power scattered per unit solid angle, for fixed incident intensity Io, wavelength $\lambda$, and refractive index m, obeys $$\frac{dP_s}{d\Omega} = \begin{cases} d^2, d >> \lambda & 1a \\ d^3, \lambda/3 < d < 3\lambda & 1b \\ d^6, d << \lambda & 1c \end{cases}$$

Equation 1a corresponds to a response in proportion to the projected area of the particle, often referred to as the geometrical limit of Mie scattering. Equation 1c corresponds to dipolar scattering, sometimes referred to as Rayleigh scattering. In the region of 1b, for $d \approx \lambda$ and for certain choices of collection angles determined by the collection optics system, the scattering response is proportional to the mass per particle, for constant material density $\rho$.

If we hypothesize that the scattered power $dP_s/d\Omega$ for a fixed number concentration N (#/cm$^3$), of monodisperse spherical particles of composition $\rho$(gm/cm$^3$), is proportional to their mass concentration $\chi$($\mu$g/m$^3$), this amounts to the following manipulation:

Response per unit mass concentration $= \dfrac{dP_s/d\Omega}{\chi} =$ $$\frac{dP_s/d\Omega}{\rho(\pi/6)d^3N} \propto \begin{cases} d^{-1}, d >> \lambda \text{ (large particles)} & 2a \\ 1, \lambda/3 < d < 3\lambda \text{ (small particles)} & 2b \\ d^{+3}, d << \lambda \text{ (fine particles)} & 2c \end{cases}$$

This simple manipulation shows that the hypothesis is asymptotically true in ($\chi$3, 3$\lambda$), by inspection of 2b. A profound result is evident: for certain ranges of collection angle, the scatter signal is proportional to mass concentration and independent of particle size, in a particle size range of practical importance. For polydisperse distributions, this result may be extended to show practical independence of size distribution provided the mean diameter lies in ($\lambda$/s, 3$\lambda$). This is recited in the parent application Ser. No. 902,510 now U.S. Pat. No. 4,249,244.

The basic relationship has been shown before but for backscattering only in the aforenoted prior art U.S. Pat. No. 4,017,186 and in the aforenoted application Ser. No. 902,510 now U.S. Pat. No. 4,249,244 for near forward scattering. (See FIG. 9 and the supporting text in the parent application).

Figure 6:
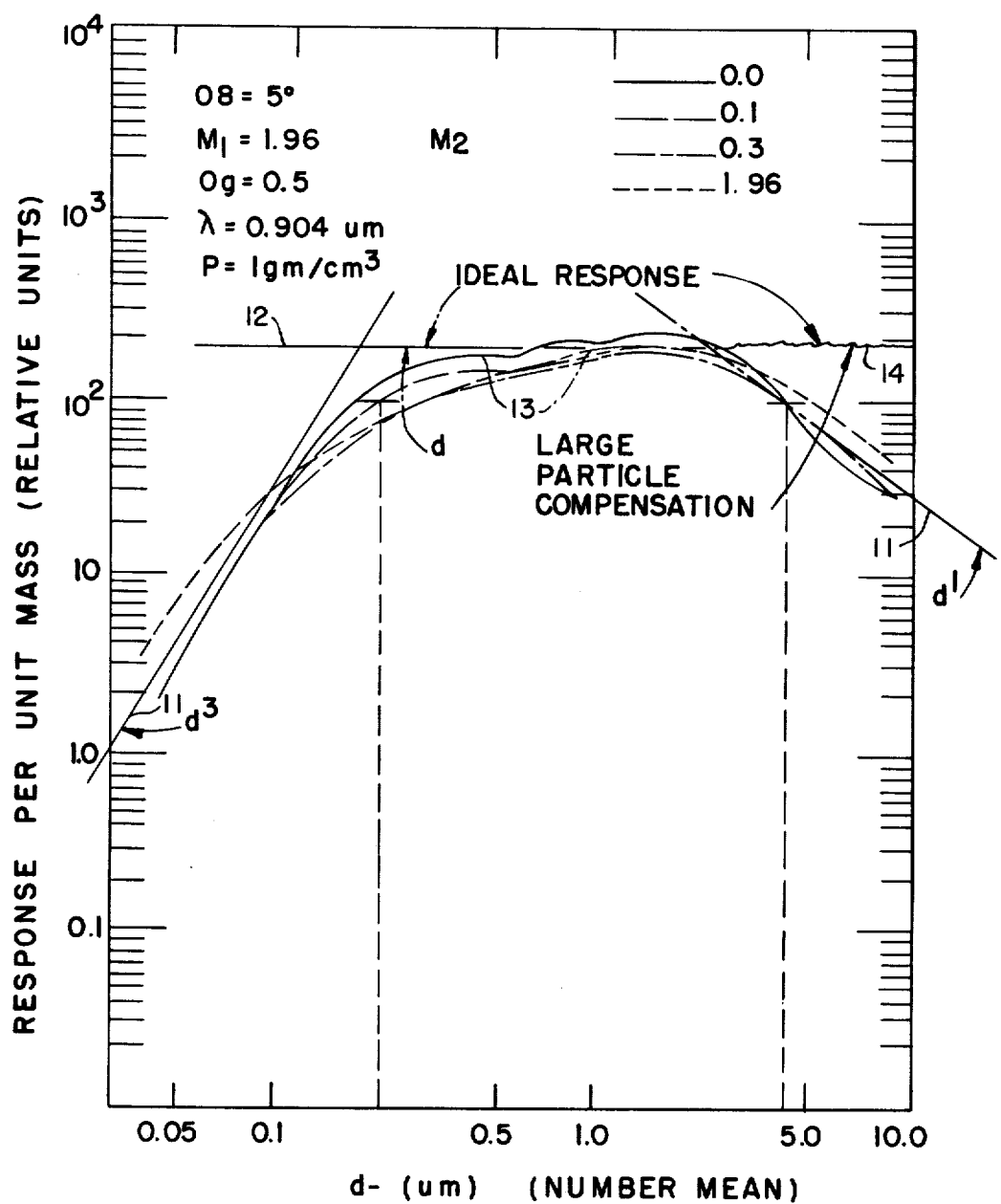
FIG. 6 shows the basic response of light-scattering instrumentation to spherical aerosols with the indicated parameters and size distributions. The figure is presented in terms of response per unit mass, a fundamentally important presentation of the Mie-scattering computations when the equipment is to be used as a mass concentration monitor.
Figure 9:
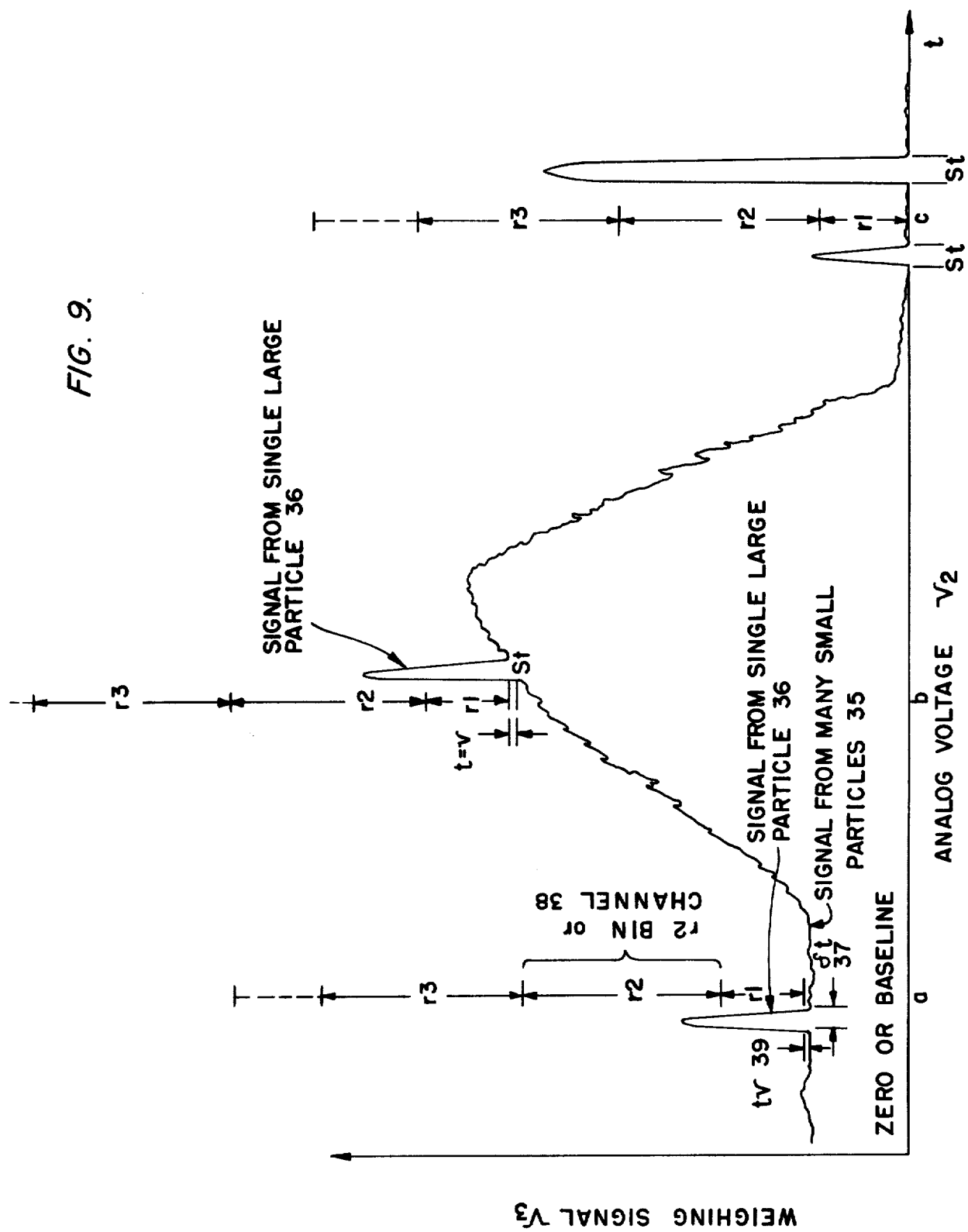
FIG. 9 shows how large particles are distinguished from small particles in terms of an analog voltage presentation.

FIG. 6, the basic data for which are taken from FIG. 9 of the parent application Ser. No. 902,510 now U.S. Pat. No. 4,249,244, shows the asymptotic relations 11 of Equation 2, the ideal response 12, and theoretical curves 13 as a function of particle size, with other parameters fixed and shown.

The ideal response 12 is a horizontal line, since the weight of the particles sensed should be independent of their size or composition. The asymptotic and theoretical responses suggest that a practical instrument can be built for dusts or aerosols with most of their mass concentration $\chi$ in the size range ($\lambda$/3, 3$\lambda$).

Outside this range, light scattering response is not proportional to $\chi$ and some form of compensation is necessary. Specifically, for large particles, $d > 3\lambda$, the underweighing nature of the light-scattering response requires an increased signal, dependent on particle size, to achieve the large particle compensation 14.

Before explaining how large particle ("d"$\geq 3\lambda$) compensation is realized, it is appropriate to note that monodisperse aerosols are very rarely found in nature of processes and even generated with difficulty in the laboratory. General aerosols are polydisperse. A commonly used distribution model for them is the lognormal distribution having two parameters, number mean diameter $\bar{d}$ and geometric standard deviation $\sigma$g, a measure of the width or dispersion of the distribution. (The equation is given in Table 1).

The theoretical Mie-scattering results of FIG. 6 are for polydisperse spherical particles in a forward scattering configuration, with scattering polar angle $\theta = 5°$. These results are included here for completeness and to substantiate the much simpler asymptotic relations of Equations 1 or 2. Note for clarity, that the range for which the response is within a factor of two of maximum is from about 0.2 $\mu$m (15) to about 4 $\mu$m (16), for this configuration.

Figure 7:
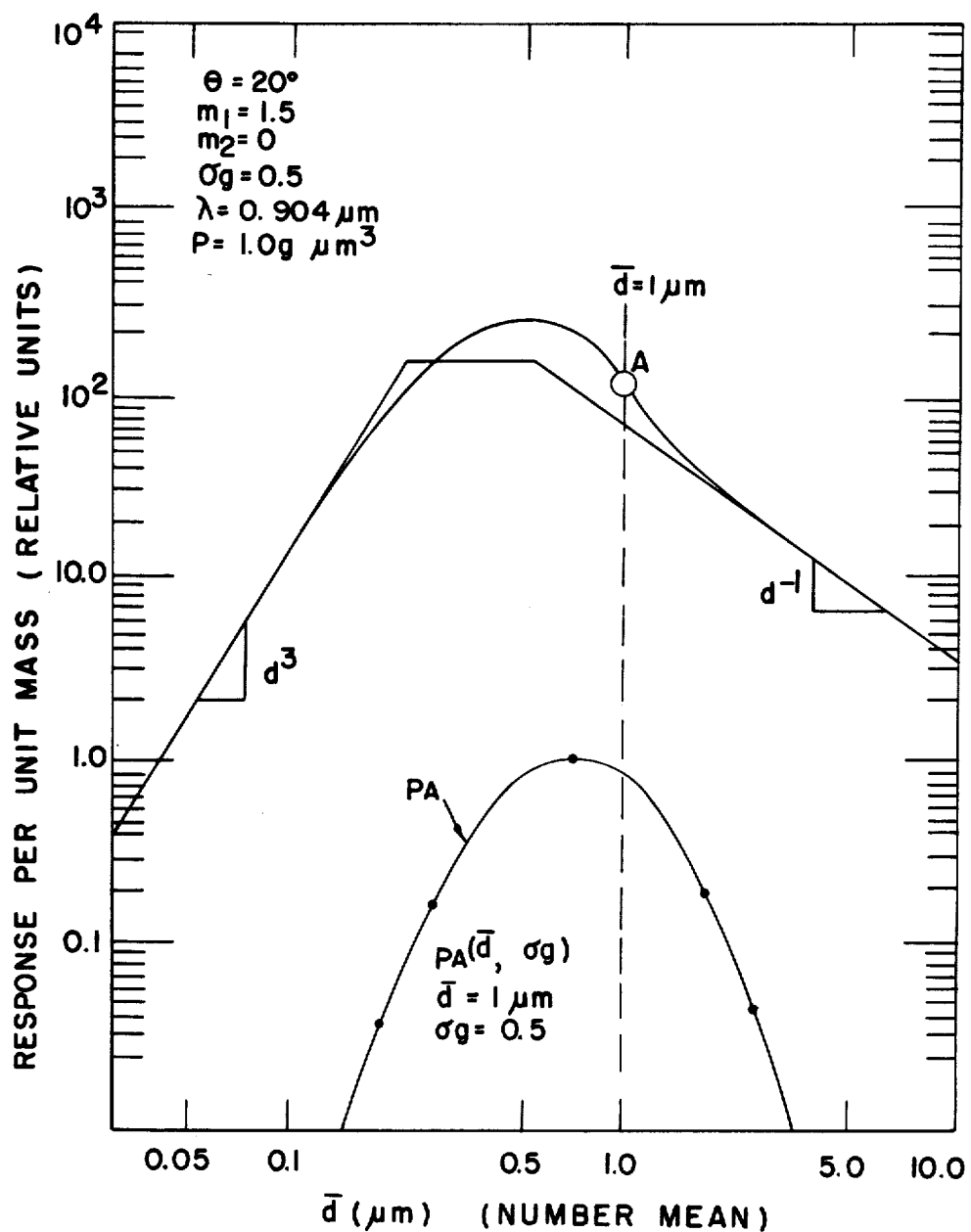
FIG. 7 is similar to FIG. 6, showing the results of light-scattering calculations for different scattering angles and, by comparison with FIG. 6, the variabilities in response per unit mass.

FIG. 7 is a similar Mie scattering calculation but for $\theta = 20°$ and nonabsorbing particles. In this case, the range for 2:1 response accuracy is reduced to about (0.2, 1 $\mu$m). Evidently, near forward scattering is superior, as far as width in the range of particle diameters is concerned. Alternatively stated, a forward scattering instrument operating around $\theta = 20°$ requires more attention to large particle compensation than one operating near $\theta = 5°$.

There are practical advantages, in some cases, to larger scatter angles ($\theta \geq 10°$) which can be "traded off" against wider response range. A major one is greater scatter signal to background or "stray light" originating with imperfect LED or laser beams. That is, there is generally less stray light at larger scattering angles, in practice.

In short, the ability to compensate for the more severe underweighing of large scatter angle instruments can provide advantages in equipment design.

Note, for emphasis, that point A (17A) is the integrated response to one polydisperse distribution $p_A(\bar{d}, \rho_g,)$ 18 = $p_A$(1, 0.5), where p is lognormal. Each point of the response curve 17 is so computed for a different distribution. The distribution chosen is representative of practice. Note, on this log-log plot, that the shape and width of the distribution does not change as a function of $\bar{d}$, i.e., movement along the abscissa.

Application of near-forward scattering proves entirely satisfactory for measurements of such predominantly spherical aerosols as oil mist, combustion products, acid mist, or other condensible mists. This necessitates that the bulk of the mass concentration is associated with particles in the $\lambda$/3 to 3$\lambda$ range. The range of 0.3–3 $\mu$m, using $\lambda \approx 0.9$ $\mu$m LED light, is important for air and workplace pollution and many process particulate monitoring applications. Instruments have been successfully reduced to practice whose response is proportional to $\chi$, under these restrictions, as recited in the initial application.

How serious is the $d^{-1}$ underweighing of prior art? And what may be done electro-optically to compensate for this inherent error?

Whereas light scattering for spherical particles is well known, it is also known that the power scattered from large nonspherical particles is sensitively dependent upon the shape and orientation of the particle as well as the index of refraction. For cotton dust and similar applications, it follows that we may be guided generally by the published information on scattering by spherical particles. Indeed, paying too much attention to such prior art or to knowledgeable and skilled individuals who rely too heavily in their judgments on the limited theory will, incorrectly, lead one away from the method we have found to work well.

Now vertically-elutriated cotton dust is a heterogeneous mixture of small and large particles. The small particle component may be described as roughly spherical. The large particle component is composed of "flaky" or "linty" particles, some of which are thousands of micrometers in one dimension, and which have highly irregular shapes and highly variable compositions.

Figure 3:
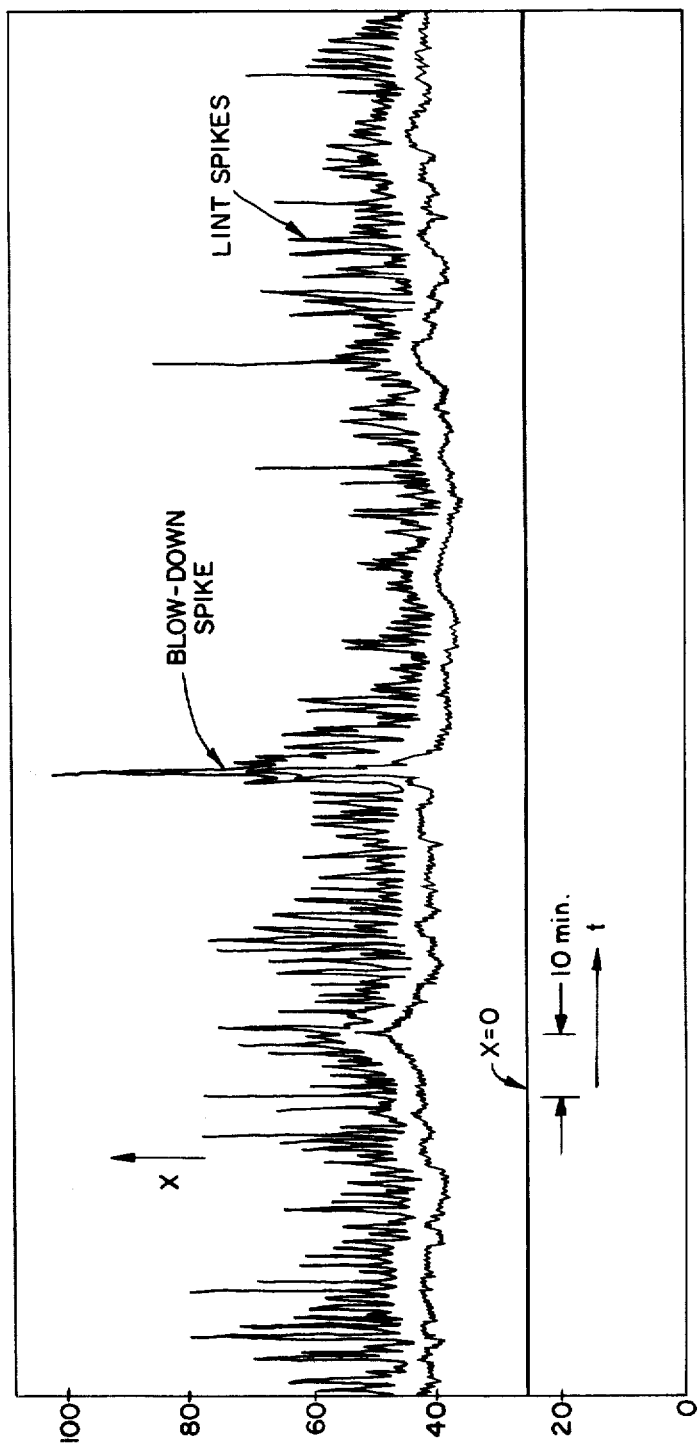

The light-scattering basis for electro-optical weighing of the VE effluent (or any particle-laden flow) is described as follows: Small dust particles, having diameter $d \leqq 3\text{-}5\ \mu m$, are known to be approximately spherical. For typical cotton dust concentrations, the number densities N are of the order of $1/cm^3$. For given $\chi$, N goes as $\sim d^{-3}$. To illustrate, if $N=1/cm^3$, $\rho=1.5$ $gm/cm^3$ and $d=5\ \mu m$, then $\chi=98\ \mu g/m^3$ if all particles were 5 $\mu m$. N increases to 125 per $cm^3$ if d increases to 1 $\mu m$, with $\rho$ and $\chi$ fixed. But because $dP_s/d\Omega \propto d3$, the total light scattered from these small particles in the weighing volume is approximately constant. Better, the collective scattering signal is directly proportional to $\chi$ and reasonably independent of size distribution.

For cotton dust, the mass concentration associated with $d<0.3\ \mu m$ is negligible. Larger particles ($d>3\text{-}5$ $\mu m$) scatter according to their area but, of course, contribute to the total mass concentration according to their volume and density $\rho$. Assume, for further illustration to reveal the severity of underweighing, that there is, in the average, one spherical particle per $cm^3$ having d-5 $\mu m$ and $\rho=1.5\ gm/cm^3$; then, as above, $\chi=98$ $\mu g/m^3$. Suppose the electro-optical gain is adjustable to indicate 98 $\mu g/m^3$. Now suppose we add one 15 $\mu m$ particle to the weighing volume, increasing $\chi$ to $$98\left[1+\left(\frac{15}{5}\right)^3\right] = 2744\ \mu g/m^3.$$

But the electro-optical response to the 15 $\mu m$ particle follows $d^2$ rather than $d^3$, so an uncompensated electro-optical system would approximately indicate $$\chi = 98\left[1+\left(\frac{15}{5}\right)^2 = 980\ \mu g/m^3.\right.$$

Clearly, even for spherical particles, some form of electro-optical compensation is required to avoid underweighing the large particles.

Compensation for large and irregularly-shaped particles may be achieved empirically. By proper design of the weighing volume size, shape, and response profile, in combination with the VE flow rate and converging slot dimensions, the small and large particles can be distinguished according to their scattering signal amplitude and frequency of occurrence.

The signal $v_1$ 19 of FIG. 5 contains sufficient information for classifying not only the large from the small particles but for classifying the areas of equivalent spherical diameters of the large particles. This classification is possible because we have discovered that proper operating conditions may be chosen such that the large particles produce infrequent but large spikes above the small particle signal.

For clarification, reconsider the above example having one 5 $\mu m$ diameter particle/$cm^3$, with $\chi=98\ \mu g/m^3$. (Recall that 125 particles/$cm^3$ with diameter 1 $\mu m$ also has 100 $\mu g/m^3$). Add a 15 $\mu m$ particle but with weighing volume occupany probability of 0.01 rather than 1 (i.e., a 1% average frequency of occurrence in the weighing volume). The average mass concentration $\chi$ increases to $98\ [1+0.01\ (15/5)^3]=125\ \mu g/m^3$. When this rare, large particle "spike" occurs, it is quite evident in the signal $v_1$. A signal increment over the 98 $\mu g/m^3$ "background" of $98=882\ \mu g/m^3$ (in equivalent mass concentration signal) occurs. Alternatively, a spike in scattered radiation of 9X the background is generated as the large particle passes through the weighing volume.

The large particles are thus easily identified and classified electronically. See FIG. 3 for a chart record example of "lint spikes". Their contribution to the mass concentration may then be determined by empirical and/or explicit calibration procedures. In this manner, the asymptotic $d^{-1}$ response is compensated to approximate the ideal.

It may also be verified theoretically that the large particles occur rarely. Table 1 gives the number density $N_i(\#/cm^3)$ for spherical particles whose diameters are above the diameter indicated by subscript, for three lognormal distributions having $\sigma_g=0.5$, 0.8 and 1. Fixed parameters are $\chi=100\ \mu g/m^3$ and $\rho=1.5$ $gm/cm^3$. $N_T$ is the total average number of particles which give the specified $\chi=100\ \mu g/m^3$.

Evidently, the large particles, which produce large responses and are easily detectable over and above the more or less constant small particle yield, occur rarely. Realization of this natural fact and implementation of electro-optical means to provide electro-optical weighing to exploit it are central to this invention.

Another natural feature included in our discovery is the insensitivity of the particle diameter above which single, large particles may be distinguished by their "spike". Using the lognormal model, with $\sigma_g=0.8$ and $\chi=100\ \mu g/m^3$, the particle diameter $d_i$ for which $N_iV_s \leqq 1$ is $d_i \geqq 2.6\ \mu m$.

If $\chi=1000\ \mu g/m^3$, $d_i$ for $N_iV_s \leqq 1$ is $d_i \geqq 5.6\ \mu m$. The basic reason for this insensitivity is the rapid decay in p(d) with increasing d, for these typical conditions. Similarly, $d_i \geqq 1.4\ \mu m$ or 39 $\mu m$, for $\chi=100$ or 1000 $\mu g/m^3$ and $\sigma_g=0.5$; and $d_i>1.7\ \mu m$ or 5.2 $\mu m$, for $\sigma_g=1.0$, for $\chi=100$ or 1000 $\mu g/m^3$.

This feature of insensitivity is also fraught with practical significance. The equipment is designed so that particles having sizes larger than some preset valve are easily distinguished for the "worst case" condition of $\chi$ and $\sigma_g$. The equipment will then work satisfactorily for less severe conditions.

We have found that a weighing volume 6 of about 1 $cm^3$ and converging slot 2 exit velocity of about 12 cm/sec permit easy identification of the rare, large particles, as shown by example in FIG. 3. The slot length and width for these conditions are about 3.8 cm and 0.6 cm, when the volumetric VE preseparator flow is about 1.85 liters/min.

Figure 20:
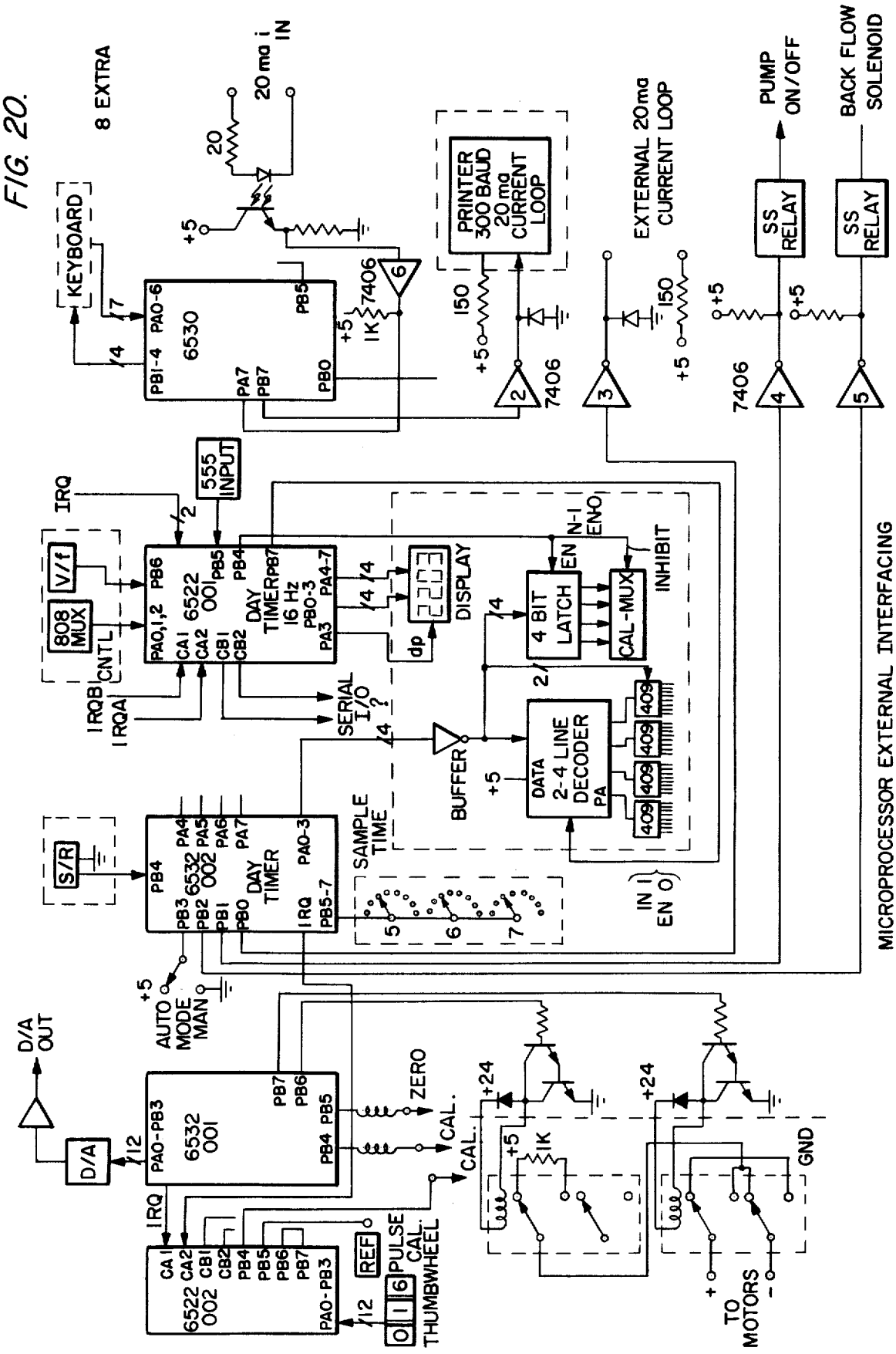
FIG. 20 is a block diagram of a microprocessor interfacing which can be used with the present invention.

Now the size of the large-particle responses (or "spikes") and their frequency of occurrence are the necessary information with which to compute their contributions to mass concentration. This may be done explicitly or, more practically, empirically. In the CAM system, the procedure is implemented with digital, microprocessor techniques, now well-known in the art as shown in FIG. 20.

The bulk of the preceeding material demonstrated the absence in prior art electro-optical instrumentation of the features of compensation for mass concentration associated with large and irregular particles and the severity of the measurement errors in mass concentration if such compensation is not included. We also outlined the experimental and theoretical basis on which we have conceived and developed this invention. Further, we show how the sampling volume and population statistics of the particles being sampled are intimately related, so that by practicing our teachings for the design of sampling volume dimension, shape, and collection optics, the large particle correction scheme may be generally applied.

The objective of any compensation is to approximate the ideal response 12 of FIG. 6. For the large particles, this amounts to "lifting" the $d^{-1}$, underweighed response 11 of FIG. 6 up to the ideal response 12.

In simplest terms, the instant invention teaches how to design and operate the electro-optical detection means so that infrequent, large particles may be sensed, with high signal-to-noise ratio, and how to correct these responses for inherent underweighing errors, when applied to mass concentration measurements. In order to better appreciate how these signals are explicitly or empirically corrected to read mass concentration, it is appropriate to examine a preferred embodiment as applied to cotton dust measurement.

Figure 8:
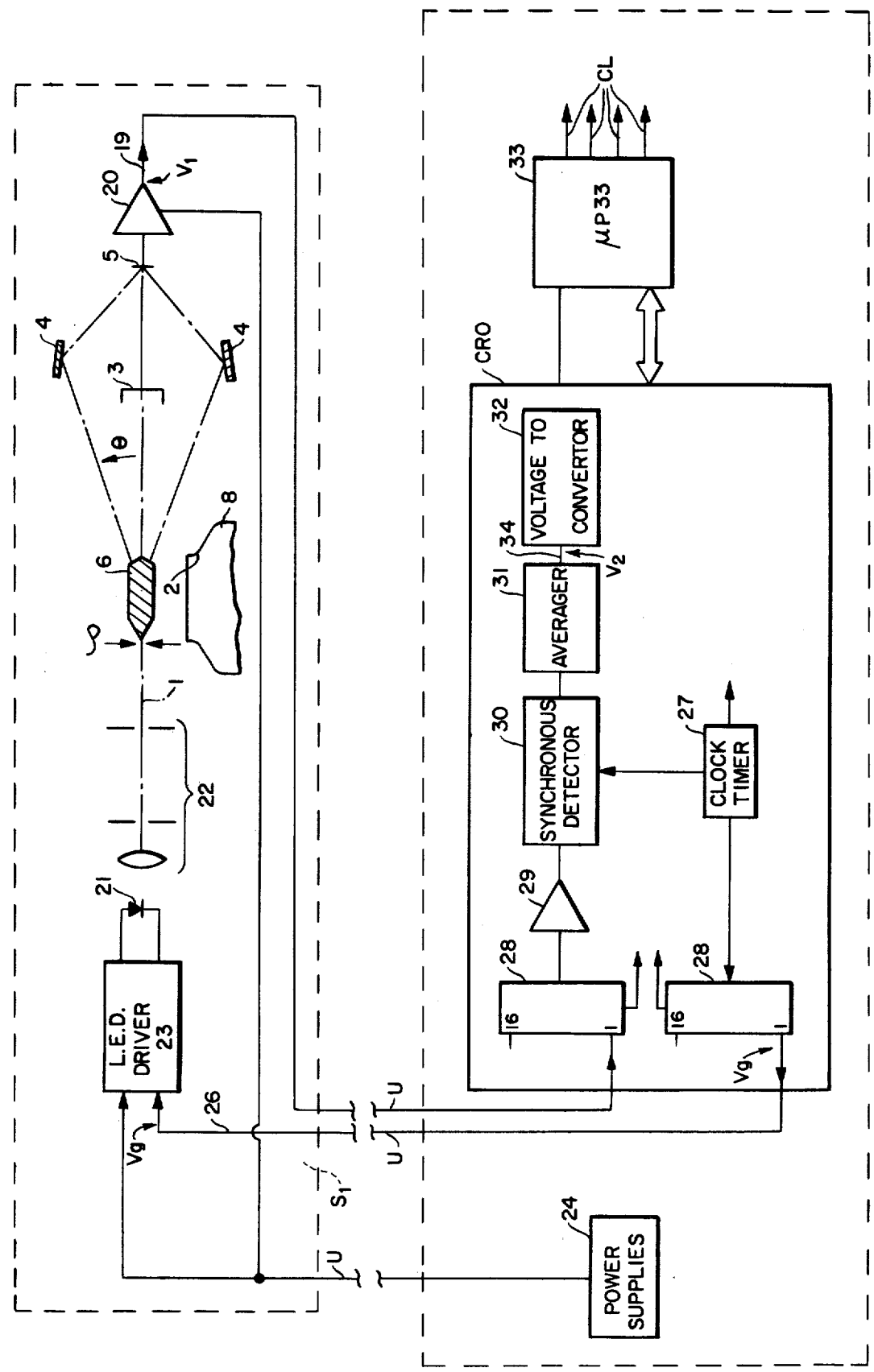
FIG. 8 is an electro-optical schematic for a preferred embodiment CAM sensor and system.

FIG. 8 is a simplified electro-optical schematic revealing how such compensatable signals are generated. The horizontal dashed lines in the figure separate the three major components of the CAM system. The sensor (shown as $S_1$) is one of multiple sensors which are serviced through an umbilical U up to one thousand feet (or even greater) in length by a control/readout unit CRO which is centrally located.

In the sensor, the LED beam 1 is generated by beamforming optics 22 which collect and collimate radiation from a light emitting diode 21. The light emitting diode 21 is in turn driven by a LED driver 23 which, in the CAM embodiment, is a single printed circuit board supplied with + and $-$DC power supply voltages 24 and a gating pulse $v_g$ on line 26. That is, upon reception of the gating pulse, the LED beam is turned on and off in a rectangular wave fashion at a rate of 10 kHz, being controlled by the interal clock timer 27 through the electronic switch 28.

Particles entrained in the effluent of the preseparator, shown in this case to be a vertical elutriator, VE 8, entertains scattering in the weighing volume 6 defined by the joint intersection of LED beam 1 and the geometric acceptance geometry of the collection optics consisting of the conical mirror 4 and detector 5. The collected radiation is converted into a voltage pulse v1 on line 19 by the preamplifier and a cable driver 20. This amplifier is similarly supplied ±DC voltages 24 through the umbilical U, from the control/readout unit CRO.

The signal on line 19 contains the particle information and passes through the uppermost of the electronic switches 28, to a post amplifier 29, then to a synchronous detector 30, to an electronic averager 31, and finally to a voltage to frequency converter 32. All of these components, their functions, and characteristics, and commercial designation and availability are well known to those skilled in the art of electronic signal processing.

The clock/timer 27 output is fed to the synchronous detector 30 and also to the microprocessor 33.

The microprocessor receives signal information from the V-F converter 32 in the form of "counts", which is optimal for digital processing techniques. This feature is central in permitting an elegant detection means; that is, simple, inexpensive, reliable, and accurate measurements result. The microprocessor software determines via control lines CL which of the multiple sensors will receive a gating pulse and deliver its signal voltage v1 on line 19 for "number-crunching".

Obviously, the signal processing just described could be accomplished without the microprocessor. As in the oil or acid mist embodiment of the parent application, the signal processing and calibration/zero techniques could be implemented with primarily analog electronic techniques. The microprocessor-based scheme recited in the instant application is far more practical and powerful.

After signal acquisition and conversion to mass concentration through explicit and empirical algorithms, the microprocessor presents its data in one of several forms, including but not limited to:

(1) a digital print-out of time-weighted averages of mass concentration for each of the sensors;

(2) a LED display of instantaneous dust concentration at any one of the sensors;

(3) an analog presentation of the dust concentration at any one of the sensors; and (4) parallel or serial digital information to central and/or higher-power computing machines for further analysis and archival storage.

As for the analog signal processing between the electronic switches 28 inputs and the voltage to frequency converter 32 output, the digital means for control, number-crunching, and data presentation are well known to those skilled in the art and it is unnecessary to recite their details here.

Although the basic temporal characteristic of the LED illumination is a high frequency rectangular wave, the net effect of the synchronous detector and averaging circuit is to produce a continuous signal v2 34 at the output of the averager circuit 31. This analog signal v2 on line 34 is generated in the ususal techniques of sampled data acquisition. Because the sampling period is very short compared to the resolution times of phenomena of interest, the signal v2 may be treated as a continuous analog voltage containing all of the essential information about the light scattered by the particles in the weighing volume.

FIG. 9 represents what is seen with an oscilloscope monitoring the averager 31 output if the gating pulse $v_g$ on line 26 were continuously applied to sensor number 1. The weighing signal voltage $v_2$ on line 34, which is in direct proportion to the light scattering voltage v1 19, is shown as a function of time. Superimposed on the more or less constant signal from many small particles 35 are rare but large signals from single large particles 36. The large particle signal is seen to have a width $\delta_t$ which is the same for all particles and represents the time of flight through the LED beam 1. The maximum height of the signal is in proportion to the projected area of the particle, according to the above arguments, in particular, those associated with Equation 1. Thus, the amplitude and frequency of occurrence of these spikes, over and above the multiple particle background is a direct measure of their size and concentration.

Consider region a of FIG. 9 where the spike is shown to fall within the r2 bin or channel #2, 38. That is, the height of the spike above the background, may be specified as falling within a channel of a pulse-type analyzer. Accordingly, since the signal from the many small particles may be readily calibrated in terms of their mass concentration, the large particle signal 36 may, after proper manipulation by the microprocessor 33, be converted to yield its mass concentration. This will be discussed more thoroughly below.

Consider now region b of FIG. 9. We have illustrated that the mass concentration due to small particles has risen dramatically. Again, since the forward scattering signal for such small particles is in good approximation to their mass concentration, the weighing signal v2 is a faithful representation of the increase in mass concentration. However, the occurrence of a single large particle is still clearly distinguishable on the same basis as a. Evidently, what matters is the contribution of the large particle over and above the small particle background. The same concept applies in part c of the figure where the background is shown to approach 0 but still there are infrequent large particles present.

The above arguments and the representation of FIG. 9 are based on continuous operation of an individual sensor, in this case sensor $S_1$. However, owing to the speed of response of electro-optical circuits, it is sufficient to sample the weighing signal v2 so that, in a time-multiplexed sense, the individual sensors are sequentially sampled at a sufficiently high rate that temporal phenomena of interest may be resolved.

A minimum duration between sample intervals is imposed by the condition that no particle be sampled twice. That is, we require that the product of the effluent velocity u and the sampling interval $\Delta t$ be larger than the LED 1 beam dimension $\delta$; i.e.

$$u \cdot \Delta t \geq \delta \tag{3}$$

Alternatively, since $\delta t =$ time of flight through the beam $= \delta/u$, $$\Delta t > \delta t. \tag{4}$$

For $\delta = 0.5$ cm and $u = 12$ cm/sec, $\delta t = 41$ milliseconds. Accordingly, in a preferred embodiment we have chosen the minimum sampling interval $\Delta t$ to be 60 milliseconds.

A major practical merit of this choice of sampling, in concert with the voltage to frequency converter may now be realized. During the sampling window, which is of precise duration w and determined by the microprocessor, the number of counts from the v-f converter will be in direct proportion to the magnitude of the voltage v2 during the sampling window. The sampling window is short compared to the time spacing between the sample windows. A representative window width is w = 3 milliseconds. Neglecting electronic transient or settling times, this permits sampling 16 sensors in 48 milliseconds, well less than the 60 millisecond duration between samples for any one sensor. This time-multiplexed sampling is basic to multisensor operation. The counts thus realized in each sampling window are readily processed by the microprocessor means and details are unimportant here.

Those skilled in the art and familiar with well-known techniques of pulse height analysis will appreciate the similarity to the digitally-implemented approach. Although, superficially, the method may appear to be that of particle size analysis with the addition of eliminating, by pre- and post-pulse subtraction techniques, the "background" signal from the many small particles, in actuality, in the instant invention we are neither producing the usual pulse height analysis function nor are we implementing single particle counting techniques. These could be achieved if desired (and have been for research purposes) but the central thrust of this invention is to generate an elegant procedure for converting the large particle responses to their associated mass concentrations, which, with the benefit of the previous discussions, we may now explain.

Figure 10:
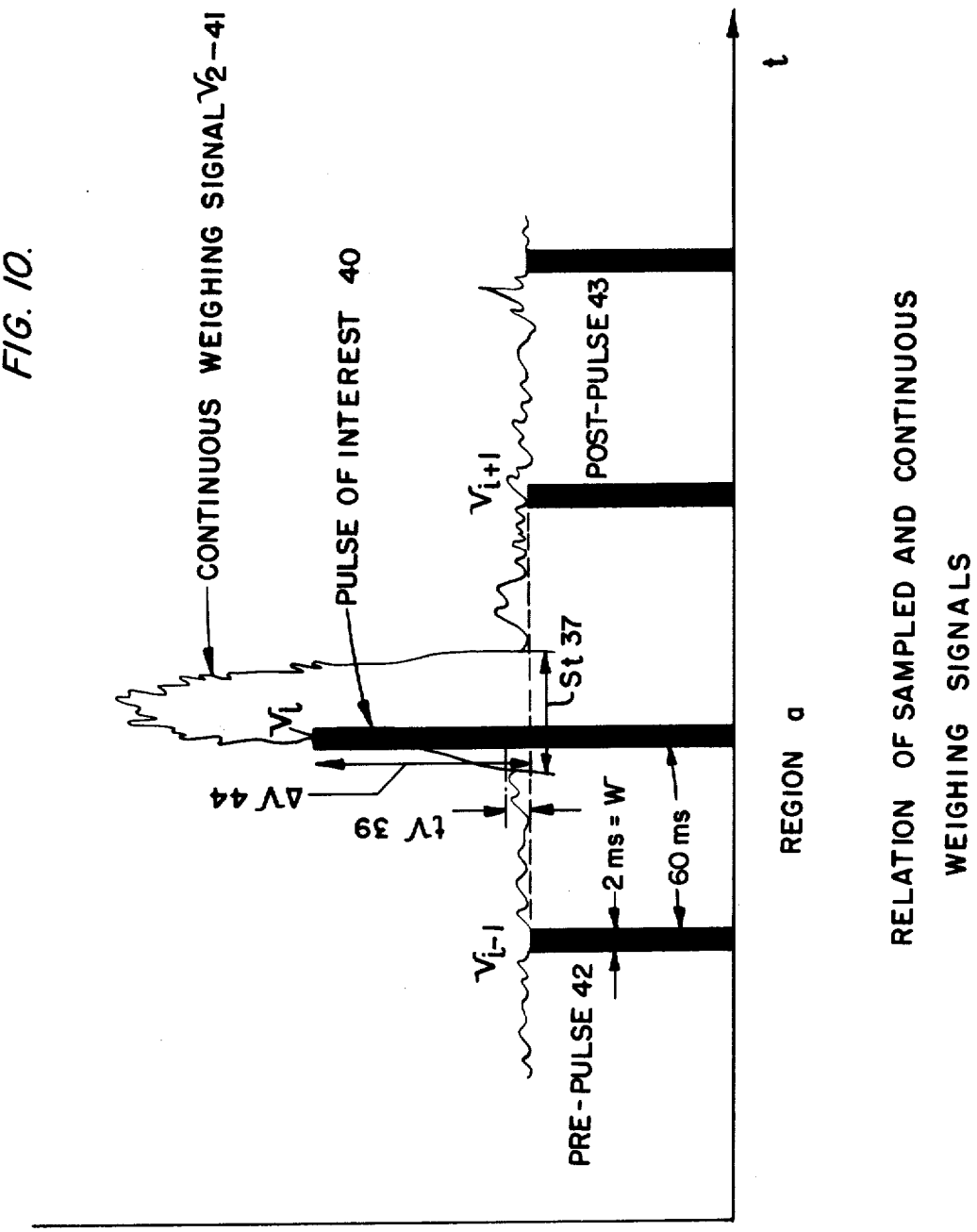
FIG. 10 shows the relation of sampled and continuous scattering or electro-optical weighing signals.

FIG. 10 shows the relation of the sampled and continuous weighing signals. Consider a sampled pulse of interest 40, which occurs randomly with respect to the continuous weighing signal v2 41. The associated pre-pulse 42 and post-pulse 43 determine the small particle background. The magnitude of the pulse of interest 40 over and above the average of the pre- and post-pulse magnitude corresponds to the sampled representation of the large particle. If the pulse of interest 40 exceeds the pre- and post-pulse average by a fixed amount tv 39, then this pulse is replaced by the microprocessor with a signal equal to the pre- and post-pulse average, corresponding to the presence of the small particles while the large particle is traversing the weighing volume. The increment $\Delta v$ 44, above the pre- and post-pulse average, is then the random sampling representation of the large particle and is subsequently processed according to its magnitude.

It is fundamentally important to appreciate the consequences of random sampling as recited in FIG. 10 and the text above. Because the sampling pulse window w is much smaller than the particle time of flight through the weighing volume, $\delta_t$, the random sample signal will range from a maximum value, when the window happens to open at the v2 maximum, to a minimum of 0, above the small particle background, when the v2 pulse occurs between two sampling windows. That the maximum or peak of the v2 pulse is not sampled and held and that some pulses are even missed is immaterial to the implementation of the algorithm for correcting the large particle spikes for their proper mass concentration contribution.

What matters in large particle correction is that representative averages of the v2 pulses are realized. The sampled pulses are classified according to their sizes. The number of sampled pulses in a given range (i.e., channel or bin) is representative of the average number of v2 pulses or particle spikes.

Now a true pulse height analysis scheme, based on peak sample and hold circuitry or their digital equivalents, will uniquely contain exactly the number of pulses in the individual channels. But this is unnecessary for our scheme, since we only require an accurate, average representation of the large particle spikes. This feature greatly simplifies the equipment with no loss of accuracy for the respponses $r_0$, 45, $r$, 46, $r_2$, 47, $r_3$, 48 and so on are utilized to compute the mass concentration. The ultimate test of the validity of such an approach is by contemporaneous comparison to gravimetric methods or even with electro-optical methods which are truly performing pulse height analysis and single particle sizing.

Another meritorious feature of random sampling beside simplication of hardware is that the mass concentration signal is insensitive to the sampling flow rate so long as it is larger than a minimum value. To appreciate this feature, first consider the small particles which generate the response $r_0$, 45 on FIG. 9. Obviously, the same scattering signal from these small particles in the weighing volume 6 of FIG. 8 is realized whether the particles are moving or not. That is, the scattering signal is independente of flow rate. It is only necessary that the particles in the weighing volume be a representative sample.

Now consider the large particles, $d>3\lambda$. Suppose that the flow rate through the sampling volume 6 in FIG. 9 in increased by a factor of 2. Then the $v_2$ signal 34 of FIG. 8 (or 41 of FIG. 10) will be of the same maximum height but the width of the pulse, $\delta_t$ 37, corresponding to the time of flight of the particle through the sampling volume, will be reduced to half its original value. In unit time, however, twice as many such particles will be sensed. If the sampling frequency and window width w are constant, the probability of sampling a given pulse is reduced by 2, but the number of pulses per unit time is increased by 2; the net result is first order independence to flow rate for the large particles, as well as the small, so long as the minimum transport velocity of Equation 3 is maintained.

This very practical feature is unknown among other types of non-electro-optical samplers, all of which respond in first order to the sampling rate or volume.

Now that the procedures for generating compensatable signals and their interpretations have been explained, we may finally describe the algorithm procedure by which the microprocessor computes the mass concentration, and in particular, corrects the responses for the large particle spikes so that their contributions to mass concentration are properly weighed.

We have found in general, that a series of terms may be used to realize the desired mass concentration signal $\chi$ $$\chi = k_0 r_0 + k_1 r_1^{n_1} + k_2 r_2^{n_2} + \ldots = \sum_{i=0}^{N} k_i r_i^{n_i} \quad (5)$$

In this series, the constants $k_i$ are the empirically-determined coefficients from contemporaneous calibrations. The exponents $n_i$ are similarly determined. The responses $r_i$ are time normalized; that is, the contents of the ith counter are divided by the sampling time, or better, the contents of a counter of the clock pulses.

This algorithm is generally and fundamentally descriptive of the basic method of the instant invention. It was necessary to describe the relatively intricate conceptual details before its discussion. The power and flexibility of the large particle compensation method and the mass concentration measurement method in general will now be explained by choosing certain specialized cases of Equation 5.

Case 1. Small Particles Only

In this case there are no large particles, so all $r_i$'s $i \geq 1$, are equal to 0 and $$\chi = K_0 r_0 \quad (6)$$

The instrument constant $K_0$ is determined by contemporaneous calibration with gravimetric devices such as vertical elutriators, open-faced filters and the like. This will be recognized as representative of the measurement methods of the initial application for oil or acid mist, for example, wherein it is required or presumed that the contributions of large particles are either zero or negligible.

Case 2. Monodisperse Large Spherhical Particles

Presume, for example, that only a single class of large particles are measured and that their response is designated in channel 4 by $r_4$. In this case, $$\chi = K_4 r_4^{3/2} \quad (7)$$

The exponent $n_4 = 3/2$ is chosen because, for spherical particles, it is known that $r_4$ is proportional to $d^2$ which is in turn proportional to the surface area. Thus, mass $\propto d^3 \propto r_4^{3/2}$. That is, there is basis from light scattering for large particles to use this exponent. This guidance may not prove to generate the most satisfactory results, for often the information about the particle characteristics are insufficient. In that case, one either determines the coefficient empirically and/or adopts the design procedure of making the channel widths for each individual response small, thus permitting use of exponent $n=1$.

Regardless of whether a guideline exponent is used or $n=1$ is chosen, the coefficients $k_i$ are determined via contemporaneous calibration.

It is instructive to recall the above arguments about averaging. Evidently, it is unimportant that the exact number of spikes or true average amplitude of a class or spikes is realized as long as coefficients such as $k_4$ are empirically determined so that accurate mass concentration readings are realized. Similar arguments apply to the effects of particle density $\rho$ (grams/cm$^3$). In other words, it is sufficient for predictions of mass concentration contributions of large particles to know the individual responses such as $r_4$ and the associated instrument coefficients, for the particles of interest.

Case 3. Small Particles and Monodisperse Large, Spherical Particles $$\chi = k_0 r_0 + k_4 r_4^{3/2} \quad (8)$$

This is an obvious combination of Cases 1 and 2 and requires no further comment for explanation. It does reveal that the instrument response linearly to the individual contributions to mass concentration.

Case 4. General Spherical Particle Size Distribution

According to the above arguments, one is guided to the exponent choice of 3/2 by theoretical considerations, resulting in a generalized response of algorithm of $$\chi = k_o R_o + k_1 r_1^{3/2} + k_2 r_2^{3/2} + \quad (9)$$

Again the individual system responses are determined empirically or experimentally. This may be done by laboratory calibration with particles of known diameter and mass concentrations or by curve fitting instrument responses to field data.

Case 5. General Aerosol Distribution with Both Small and Large Irregular Particles It is unnecessary and probably incorrect to use the 3/2 exponents in the general case. This necessitates use of the general algorithm of Equation 5. As for the spherical particle case, experimental and explicit means for the determination of exponents, if other than 1, and instrument coefficient $^s k_i$ must be used.

We can now recite certain practical cases wherein the general algorithm may be simplified.

Case 5a

A recommended procedure is to choose $n_i = 1$ for all classes and to compute $\chi$ according to $$\chi = k_o r_o + k_1 r_1 + k_2 r_2 + \quad (10)$$

In this equation, the individual coefficients $k_i$ are chosen such that the accuracy of the algorithm in predicting mass concentration is maximized. That is, contemporaneous measurement with gravimetric techniques over a wide range of process or environmental conditions will, through various choices of $k_i$, minimize the errors in the algorithm's predictions. Also, different channel widths for the various $r_i$ response classes may result in better accuracy.

The experimentalist is not totally left to "cut and try" procedures for $k_i$ determination. Other information and experience will guide him in the choices of these coefficients. For example, in some processes, most of the mass concentration in associated small particles with only one or two response classes $r_i$ necessary. Independent measurement means may be used to separate the small and large particles. All such additional information provides guidance in the choice of the k1, k2, etc.

In any case, and by whatever means achieved, the ultimate objective is to make the predictions accurate relative to some accepted, usually gravimetric, measurement means.

Case 5b

In the special case of cotton dust measurements, wherein the particles large, irregular, and predominantly fibrous in nature, and where a vertical elutriator is used (primarily for OSHA compliance purposes) to preseparate, we have found that surprisingly accurate results may be obtained with a two-term algorithm as shown:

$$\chi = k_o r_o + k_1 r_1 \quad (11)$$

Indeed, as shown in FIG. 4, such a simple algorithm has proven to duplicate the readings of the vertical elutriator gravimetric method within better than ±25%, for 95% of the time.

As a matter of information for the interested reader, much of our experimental and exploratory work with algorithm utilized 9 particle spike classification channels. Although this large amount of size and classification information shed considerable light into the nature of cotton dust the accuracy of more elaborate algorithms were generally only slightly better and in some cases worse than the simple algorithm of Equation 11.

Evidently, the ability to generate representative average information of the large particle contribution is a powerful and general electro-optical measurement method. It will be recognized that this information may be manipulated via other algorithms to achieve other objectives than predicting mass concentration. We now recite three such applications.

Use of preseparators with electro-optical measuring equipment introduces measurement and maintenance difficulties and in some cases intolerable errors. It is very desirable to simulate penetration efficiencies for such preseparators; this can be done electro-optically with ease.

The reason to simulate consider penetration efficiencies simulation is that it is well known that there are large particles in workplace or process aerosol distribution which are of no interest or produce no undesirable health effects. It is, therefore, desirable to exclude them from the measurement. This, for example, is the basic purpose of the vertical elutriator; particles having aerodynamic effective diameters larger than $15\mu$ are supposed to be excluded from the sample. However, it is well known that the vertical elutriator effluent contains particles which are much larger than 15 $\mu$m both in aerodynamic effective diameter, and in one major dimension of large irregular particles. The latter is particularly true for fibrous materials, for it is common to find fibers having hundreds or even thousands of microns in length in the effluent of the vertical elutriator.

If it is desired to exclude such particles from the electro-optical weighing procedure, it is trivially implemented via minor modifications to the mass concentration algorithm. To illustrate, suppose the subscript i in the following equation corresponds to the size class represented by equivalent spherical diameter particles of the diameter $d_i$.

$$X = K_0 Y_0 + K_5 Y_5 + K_{10} Y_{10} + \quad (12)$$
$$K_{15} Y_{15} + K_{20} Y_{20} + K_{25} Y_{25} + \cdots$$

Now suppose it is desired to simulate some preseparators penetration efficiency F(d) as follows:

$$F(d) = \begin{cases} 1, & d \leq 5 \ \mu m \text{ class} \\ 0.8, & 10 \ \mu m \text{ class} \\ 0.5, & 15 \ \mu m \text{ class} \\ 0.2, & 20 \ \mu m \text{ class} \\ 0, & > 20 \ \mu m \text{ class} \end{cases} \quad (13)$$

Evidently, this penetration efficiency or characteristic curve permits complete collection of all particle less than 5 m and no collection of particles largaer than 25 $\mu$m, with intermediate collection allowed for particles in between. Such a penetration efficiency is grossly representative of the vertical elutriator.

Now, in the absence of any preseparator, a CAM sensor would measure total mass concentration according to Equation 12. Its response, with a preseparator described by Equation 13, would be simply generated by:

$$\chi = k_o r_o + k_5 r_5 + 0.8 k_{10} r_{10} + 0.5 k_{15} r_{15} + 0.2 k_{20} r_{20} \quad (14)$$

Obviously, this is a powerful simulation tool for may respireable and other dusts. Further, any penetration efficiency, even artificial ones with fractions greater than unity for certain classes, could be generated if desired.

Specifically, note for possible applications of cotton dust measurement, that the weight contributions of particles larger than 15 μm may be easily excluded from the measurement by settling all coefficients k for particle classes larger than 15 μm=0.

Case 7. Mass Fraction

For analysis of aerosol effects and particularly for determination of performance of control equipment or health effects, it is frequently helpful to have approximate mass distributions. That is, for example, the expense and complexity of dust suppression equipment is sensitively dependent upon the amount of mass associated with small or large particles; it is much more difficult to remove the small particles.

For example, easily implemented manipulation of the basic data from the mass concentration algorithm is to provide the mass fraction F15, given the amount of mass concentration associated particles larger than 15 μm. This could be computed according to the following exemplary form:

$$F15 = \frac{X_{15}}{X} = \frac{\frac{1}{2}k_{15}r_{15} + k_{20}r_{20} + \cdots}{\sum_{i=0}^{N} k_i r_i} \quad (15)$$

The factor ½ on the initial term orginates because of the assumption that the $r_{15}$ channel has effective diameter equal to 15 μm as its center.

Evidently, any other mass fraction could be similarly computed.

The power and flexibility of the algorithm procedure is not limited only to predictions of mass concentration. Given the basic information, other important aerosol parameters may be measured.

Reconsider Equation 1 and note that the instrument response $r_i \propto d_i^2$, $d > 3\lambda$. This has the obvious interpretation that the electro-optical response is proportional to the surface area of the particles. According to the same arguments as for mass concentration, the surface area per unit volume or surface area concentration is similarly measured, having dimension of m² of surface area per m³ of effluent. For large particles, this response is more fundamental for optical systems than mass concentration response.

Surface area per unit volume,, designated S, is important in chemical reaction rates, such as explosions or evaporation, and is a fundamental parameter of aerosol mechanics. Prior to the instant invention, it has not been possible to provide a direct measure of this parameter.

Extending simply from the above arguments, we provide an analogous algorithm for surface area concentration:

$$S = C_0 r_0^{n_0} + C_1 r_1^{n_1} + \ldots = \sum_{i=0}^{N} C_i r_i^{n_i} \quad (16)$$

In this case, there is good theoretical and experimental evidence to choose the coefficients $n_i = 1$, for i greater than 1.

Automatically-Compensating Traceable Calibration of the CAM

Figure 2:
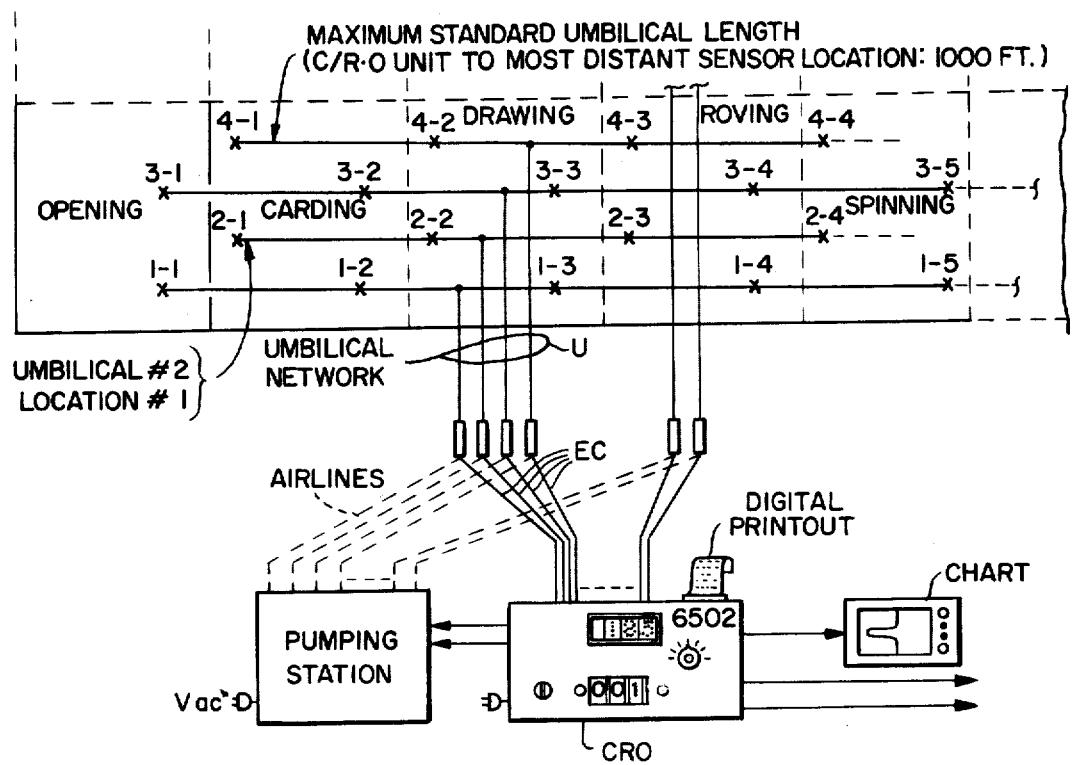
Figure 11:
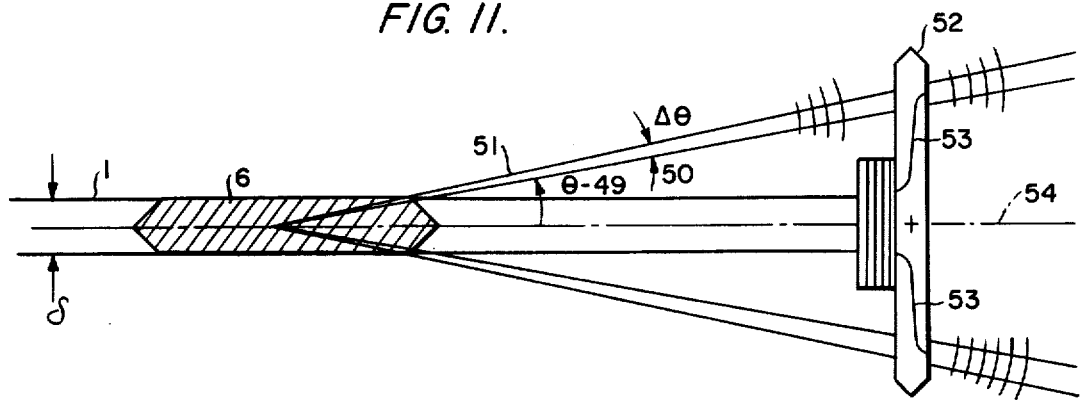
FIG. 11 shows the calibration/zero element means of the parent application.

FIG. 11 shows the calibration element recited in the initial application and is essentially the material given in FIG. 2 of that application. Referring to FIGS. 5 and 11 of the instant application, it is seen that the mutual intersection of the LED beam 1 and the collection optics typical system 4 and 5 similarly, as in the initial application, define a scattering or weighing volume 6. Representative light rays collected at mean angle θ(49) and angular rage Δθ(50) constitutes a collection cone 51, a representative one of which shown emanating from the center of the weighing volume and thence the collection optical system. The calibration zero element 52 of FIG. 11 is shown in the calibrate position wherein the signal light is blocked and a precisely known fraction of light from the main beam 1 is inserted into the optical system by means of optical fibers 53 and thereafter collected in the same manner as signal light. As recited in the initial application, this permits calibration of the entire optical system.

As also recited in that application, the calibration signal is used to compensate automatically the entire electro-optical train for changes in the LED beam power, detector, amplifier sensitivity, mirror or lens transmission, and the like. Evidently, once the calibration signal is generated with the calibration element means recited in that application, it is a simple matter for those skilled ordinarily in the art to design means to automatically correct the system transfer function for gain. This may be done by either analog, combination analog and digital, or strictly digital techniques.

Upon 180° rotation about the indicated axis of rotation 54, the calibration element is in the zero position wherein the signal light is blocked. This constitutes a baseline signal which is similarly used to automatically compensate the electro-optical transfer function. Again, analog, combination analog and digital, or digital techniques may be used. Finally, the calibration element may be exchanged or compared to a standard element, thereby permitting traceability of the calibration.

All of these features have been recited in the initial application. Their inclusion here is to provide continuity in the improvements we have realized for application to more general dust or aerosol concentration measurements.

In general, the operation of the calibration element is to receive, in the calibrating position, part or all of the main beam power which is representative of the intensity falling on particles when they are in the weighing volume. Since the attentuation by particles under normal mass concentration measurements is very small, the intensity falling on the diffuse scatterers and attenuators 55 contained in the calibration element is quite accurately representative of the intensity in the weighing volume. The function of the diffuse scatterers and attenuators 55 is to inject a known and stable fraction of the main beam into the optical system. In the initial application, this was done by the convenient means of fiber optics. Other means may be readily appreciated and have been used, for example, in some of our acid mist monitoring work. In this work, because the mass concentration signals of interest were much higher than the oil mist, it was possible to use a mirror system rather than fiber optical system for generating the requisite higher calibration signal. In general, the higher the mass concentration signals of interest, the higher the calibration signal should be, for compatability in span.

Extensive field experience with the forward scatter monitor in use for measuring mass concentrations and with the calibration/zero concept has taught that the fundamental concept is sound and practical. Indeed, measurements have been made with embodiments of the initial application which were heretofore impossible. However, experience and further testing has taught several improvements in the method.

One such improvement is the feature of generating a process zero, as opposed to generating a zero electro-optically. Process zeroing is accomplished by supplying particle free fluid to the weighing volume. Although this is not always practical, in some situations it is relatively easy. When process zeroing is practical, we have found simplified operation and superior accuracy in reproducibility of the zero baseline.

Yet another improvement found necessary in a few situations is the requirement for large dynamic range in the measurements. For example, in acid mist work, the concentration of particulates upstream and downstream of the demisting equipment is different by a large factor, perhaps, in some cases, 100. Thus, in order to use the same electro-optical train in such wide dynamic range circumstances, it is desirable to have multiple calibration elements so that the calibration may be produced for each range of interest. This enhances reliability and accuracy and retains the essential concepts of the initial application.

Figure 12:
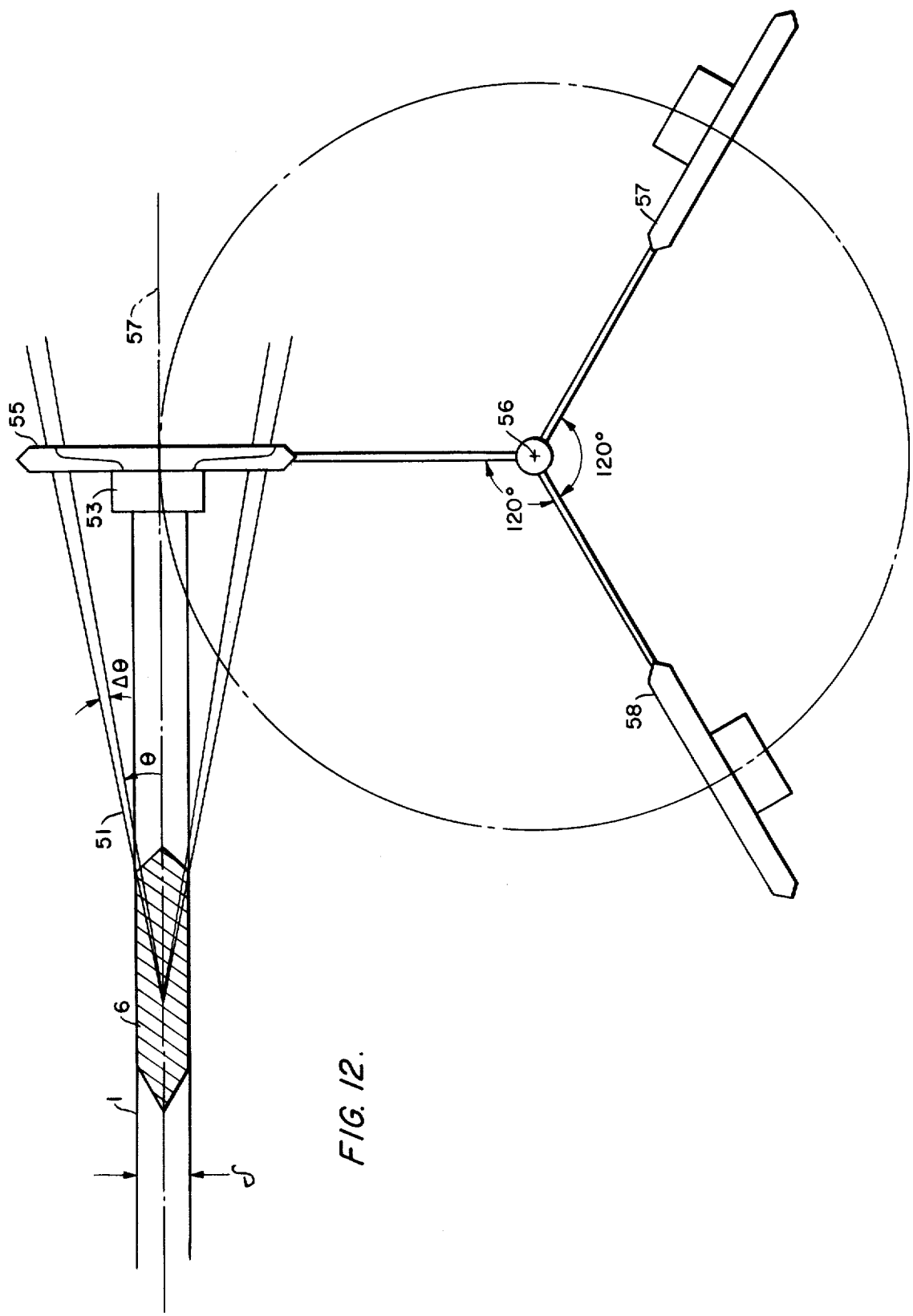
FIG. 12 shows a calibration/zero element with multiple calibration elements and one zero element rotationally positioned in the beam.

FIG. 12 shows an improved means of rotation positioning multiple calibration and/or zero elements. In this case, calibration element #1 55 is rotated about an axis 56 which is disposed of the side of the optical axis 57. Again, the calibration element 53, as shown in FIG. 11, is indicated in the calibration position. Calibration element #2 57 could then be used for a higher or lower range of measurements. The elements may be rotated synchronously with angular sensing by electro-optical or magnetic means. This permits automatic ranging over wide dynamic ranges of measurement.

Element #3-58 could be another calibration or a zero element for generating electro-optical zero baseline, as in the initial application. If process zero is used, the zero element might be omitted.

Clearly, almost any number of calibration elements and/or zero elements may be used by this displaced axis of rotation. Still further, the axis of rotation could be parallel to the optic axis 57 and permit an even larger number of calibration and/or zero elements.

Such configurations as FIGS. 11 or 12 permit the calibration element to be displaced between the weighing volume 6 and the final collection optical system. This is often necessary if the process fluid pressure or temperature are incompatible with the environment for the calibration element or the rest of the electro-optical system. That is, it may be desirable in some cases to place a window between the weighing volume and the calibration element. Similarly. a window(s) may be placed to the left of the weighing volume, between the weighing volume 6 and the LED beam forming optics, as in FIG. 11 (see FIG. 2 of the parent application) When this arrangement is used, it is evident that the function of the optical fibers 53 in FIG. 11 is to collect the light following the diffuse scatterers and attenuators 55 and displace it transversely for injection at the proper place into the collection optical system.

Figure 13A:
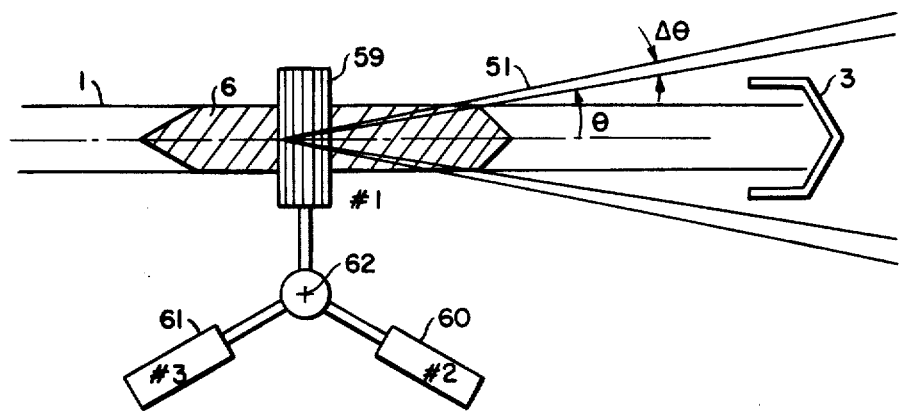
FIG. 13 shows a similar calibration element rotationally positioned in the beam, but in this case within the sampling volume, rather than exterior to it as above.
Figure 13B:
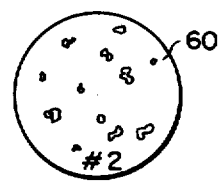

When the process fluid is compatible with the calibration/zero element, a simplification and significant improvement in function may be realized by placing the calibration elements as shown in FIG. 13. The calibration element is rotationly positioned near the center of the weighing volume. The diffuse scatters and attenuators are implemented precisely as before but in this embodiment it is unnecessary to have the fiber optics (or mirror) for transversely displacing the calibration light signal, for the collection optical system inherently accepts them in this position within the weighing volume.

Another feature of this multiple element method is that rather than using diffuse scatters and attenuators for generating the standard signal, a particle or particles in the size range of interest may be used. This would be particularly useful for large particles. For example, if a single large particle were placed on calibration element #2 60 then its response would be indicative of the large particle spike discussed above.

In some cases, to achieve averaging over several particles, it might be desirable to contain several particles in this same size range. Evidently, with the three calibration elements shown, particles in one size range could be placed on element #2 60 and yet another size range could be placed on element #3 61.

Another alternative for the multi-element calibration is that all three might be diffuse scatterers for wide dynamic range or all three might contain particles in different size ranges to generate the different spike responses recited above.

Another combination for the three elements would be, for example, to let element #1 59 of the diffuse scattering element to calibrate the equipment for small particle mass concentration. Calibration element #2 60 would contain a particle or particles in the size range of interest, and calibration element #3 61 would contain only the glass interfaces necessary to contain the particles. Particularly if the particles are small, it would be desirable to measure the glass scattered background by this means.

In building a field-worthy measurement apparatus, it is generally advisable to simplify. We have found, in the cotton dust embodiment, that a single calibration element as recited in FIG. 14 has been entirely satisfactory to perform both the small and large particle calibration simultaneously. That is, the calibration element 64 employs, as one preferred embodiment, multiple layers of course grain, black and white photographic film, such as Kodak Tri-X. The film is exposed to varying degrees, but usually toward high opacity and is processed normally.

Figure 14:
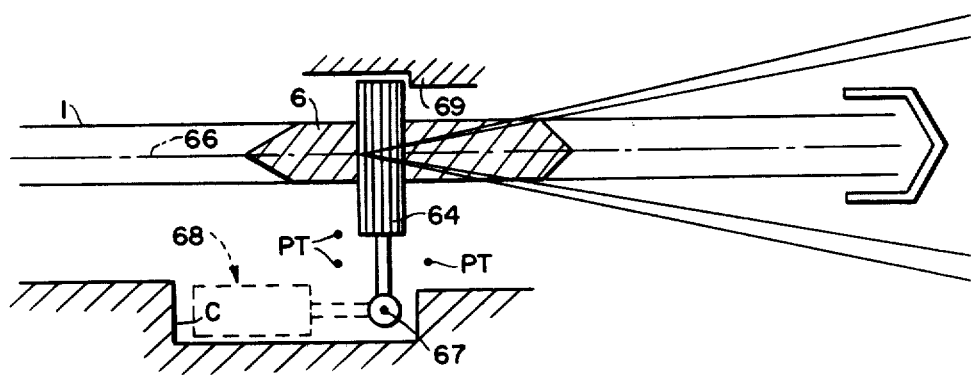
FIG. 14 shows a specialized refinement of the traceable calibration scheme as used in a preferred embodiment of the CAM sensor for cotton dust measurement.

In the embodiment shown in FIG. 14, the particle trajectories PT are normal to the paper, say upward, parallel to the axis of rotation of the calibration element 64, and perpendicular to the electro-optical axis 66. A process zeroing approach has been found to be most effective for this measurement and is accomplished by flowing particle free air from a highly efficient filter through the weighing volume.

The calibration element is rotationly positioned above the axis of rotation 67 and, when not in use, is rotated into a STOW position 68, a protected cavity C provided in the wall of the flow cell. Note that the STOW position removes the calibration element from the flow of sampled air. In this case, the aerodynamic converging slot would be just below the weighing volume 6 in FIG. 14.

In this embodiment, the rotational motion is achieved with a small DC motor. Clockwise rotation of the element from the STOW position is permitted until the element hits the stop 69 provided in the opposite wall of the flow cell 69. After the calibration, which typically takes a few seconds and is performed typically each one or two hours and during a process zero, the element is rotated counter clockwise about the axis of rotation 67 to the STOW position 68.

The rotation means and STOW location of FIG. 14 have proven entirely satisfactory for such nominal environment as cotton dust and the like. Should the environment be more adverse, then the straightforward extension would be to rotate the element further away from the sampling volume and/or cover it with a protective door. For hostile process fluids, of course, one would return to the calibration/zero procedures recited in FIGS. 11 or 12.

Figure 15A:
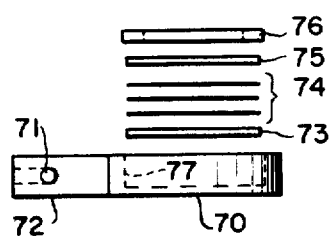
FIG. 15 shows the calibration element of FIG. 13 in detail.
Figure 15B:
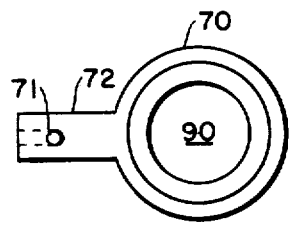

FIG. 15 shows the detail of a single calibration element, multiples of which might be used on the same axis or on multiple axes of rotation in a given application. The element consists of an aluminum body 70 and means 72 for securing the body onto an axle or shaft 71 of a DC motor or other rotational means.

A cylindrical bore 77 is machined and the calibration element components are therein inserted. These components consist of a first glass window 73, the calibration means itself, such as diffuse attenuators (e.g., exposed film), or a particle or particles of interest, 74. A second glass cover 75 completes the sandwich, all of which is held in place with a pressed-in retainer ring 76.

Figure 16:
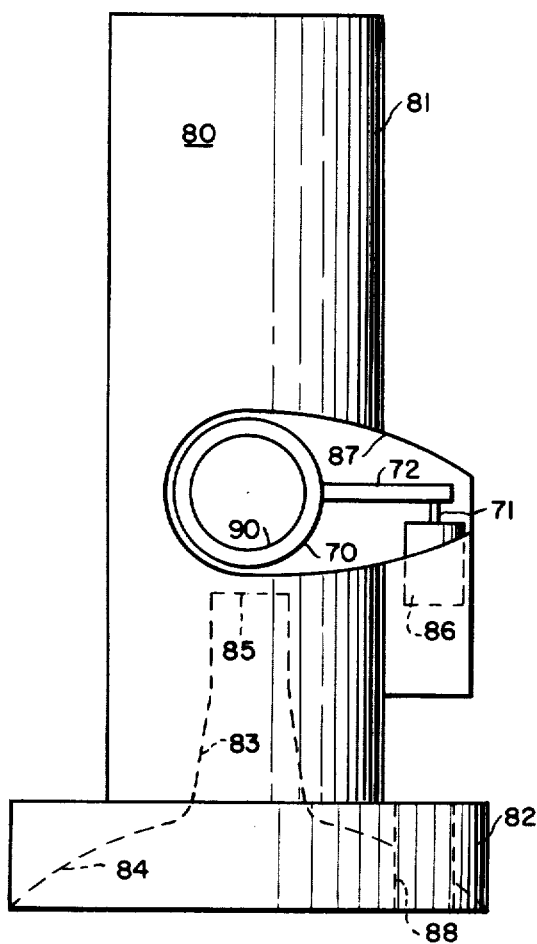
FIGS. 16, 17 and 18 are front and side elevational views and a bottom view, respectively, of a flow cell shown diagrammatically in FIG. 5 and adapted to support the electro-optical CAM sensor.
Figure 17:
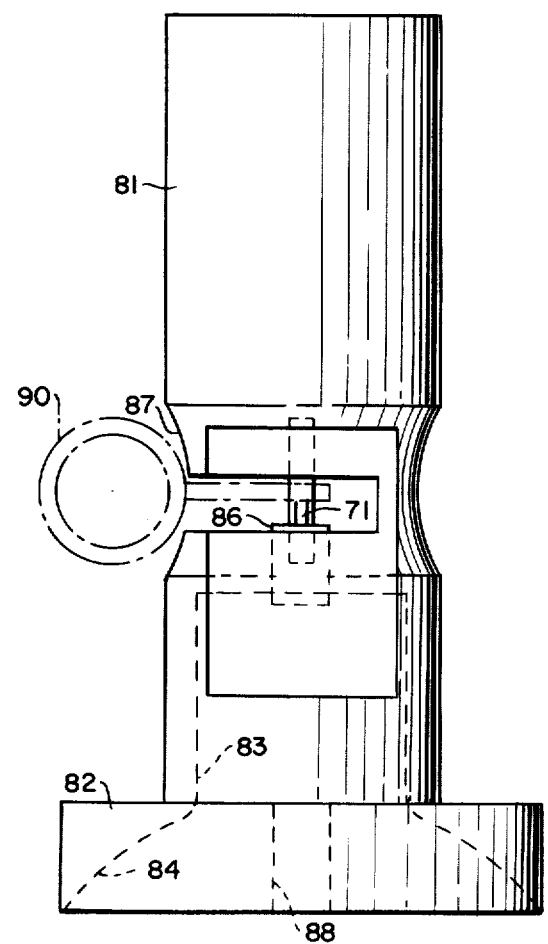
Figure 18:
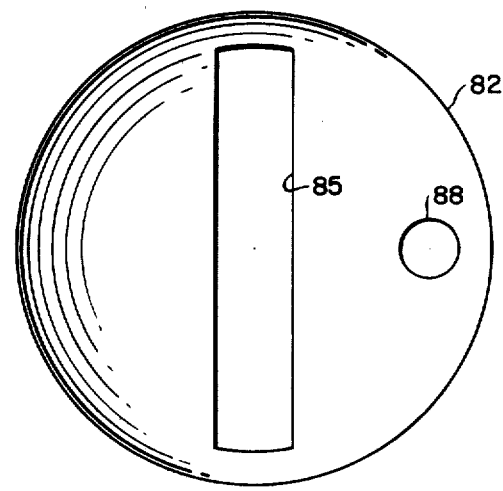

FIGS. 16–18 illustrate a flow cell 80 adapted to support a calibration element 90 of the type shown in FIG. 15. Cell 80 comprises a shell 81 and base 82 having internal lower surfaces 83, 84, as shown in FIGS. 16 and 17, shaped to correspond to the aerodynamic configuration 2 of elutriator 8. The surfaces 83, 84 thus terminate in a collecting slot 85 adapted to be disposed immediately below sampling volume 6. Element 70 is mounted to motor shaft 71 of DC motor 86 via arm 72. Shell 81 includes a central arcuate CAM opening or passage 87 which permits the diffuser or calibration element 90 to be rotatably pivoted in position so as to intercept beam 1 within the sampling volume 6, as shown for example in FIG. 14. Motor 86 is convenientl supported to one side of the shell in any suitable manner and base 82 is provided with an opening 88 axially aligned with the motor through which access to the motor may be gained.

As a general rule, the holes in the body and in the insert ring are typically about 1.5 to 2.0× the diameter of the laser or LED beam.

It is obvious to those skilled in the art that various forms and types of calibration materials may be used.

It is also evident that the teachings about traceability of the calibration scheme and the procedures by which the electro-optical transfer function is corrected for both gain and zero baseline shift faithfully follow the teaching of the parent application and need no further recitation here.

We do note, for emphasis, that the means of generating a zero signal by electro-optical means or by process flow means are treated identically with the automatically-compensating circuitry.

The motivation for the CAM system measurements is to measure the respirable dust to which workers are exposed. The multi-sensor CAM system is a cost-effective continuous area monitoring means. Area monitors, which are stationary, are to be distinguished from personal monitors, which are carried by the workers. There is now and probably always will be raging controversy between the relative merits of area vs. personal sampling to determine worker exposure. Area monitoring has in its favor more accurate representation of the performance of the engineering or dust controls. Personal samplers are more representative of work practices. It is not clear which is better representative of what the worker breathes.

Figure 19:
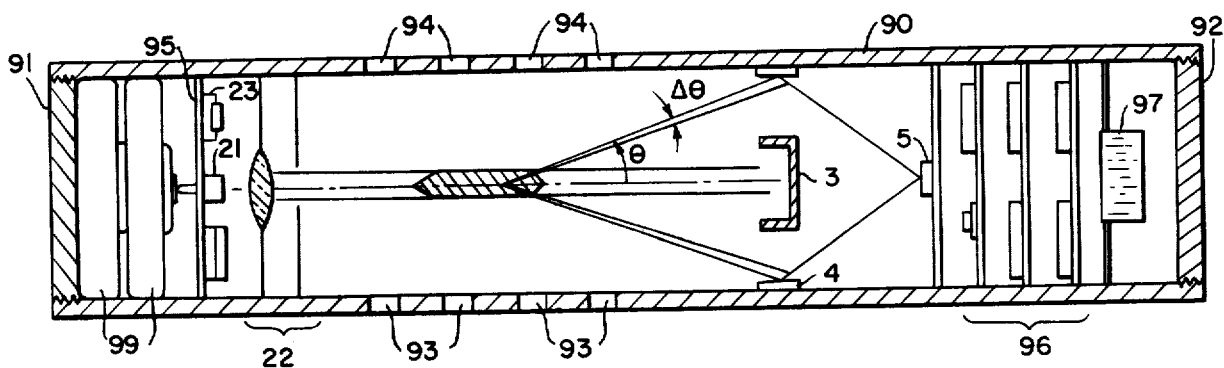
FIG. 19 shows a miniaturized packaging of the CAM, the "MICROCAM".

Fortunately, the methods of the CAM sensor system, including data processing, may be miniaturized and may be similarly applied to personal sampling as to area monitoring. FIG. 19 shows a MICROCAM which would be worn by a worker. It is completely portable.

A miniaturized portable personal sampler of this type is adapted to be worn by a worker exposed to the air being monitored and includes a housing 90 within which the electro optical elements of the sensor, such as shown in FIG. 8 are housed. Housing 90 includes access openings at opposite ends which may be conveniently capped by caps 91, 92 after the components of the sensor are mounted inside. As shown in FIG. 19, intermediate the ends of the housing there are provided a plurality of air flow holes 93,94 disposed on opposite sides of the housing of the sampling volume 6. The light emitting diode (LED) 21 is suitably mounted to a circuit board 95, along with LED driver 23 and positioned adjacent the beam forming optics 22. The signal processing and data processing circuits 96 are packaged on conventional circuit boards with the outputs conveniently terminated at connector 97 to provide convenient read out. Access to connector 97 is gained through cap 92. Power to the various circuit boards are provided by batteries 99. It will be readily apparent that air flow through holes 93, 94 which occurs as the worker carrying the personal monitor walks about the monitored area enables the area to be continuously monitored.

While the various components of the electro optical system are readily available and commercially available for convenience, FIG. 20 is included to illustrate external interfacing for the microprocessor 33 with circuit boards illustrate either by their commercial designation or conventional function.

There are three features of the CAM method recited above that are noteworthy in their uniqueness and in their ability to generate cost-effective worker exposure.

(1) Insensitivity of measurement to sample flow rates

The practical effects of this result are profound: it is unnecessary to have a heavy and power consumptive pump to drive a precisely described flow. For the MICROCAM, convective currents produced by worker motion, probably even when asleep, will assure random sampling of the particle population.

2. Particle sizing and classification features

The large particle spikes, similarly as for the CAM, may be classified according to their average size and stored in the signal processing and data storage parts of the MICROCAM. This permits weighting of the large partaicles according to any penetration efficiency.

3. Complete solid state electronics with no moving parts

Recent developments in efficient LED sources, detectors and in electronic amplification and storage circuitry represent a technological innovations that make the MICROCAM practical.

Traceable and automatically compensating calibration zero concepts apply to the MICROCAM also but on a different time scale. In the MICROCAM embodiment, the worker removes the unit from a master unit at the beginning of his work shift. Upon completion of his shift he returns the MICROCAM to the same receptacle. He removes the end cap which exposes the female connector and connects it to the master unit. Upon insertion, the data acquired during his shift are dumped into the master unit which processes the data and prints out the results of interest. These results may be used for legal and archival purposes as well as worker notification or other administrative and engineering uses.

While the MICROCAM is in the master unit, its batteries are charged and its performance investigated. More specifically, its zero baseline and sensitivity are determined and stored for computations. If the unit is not performing satisfactorily, annunciation is made.

Calibration may be achieved by insertion of a calibration element, precisely as is according to the teachings of the initial and instant applications. Or further, while in the master unit, clean air and calibration particles may be supplied to the unit while in its receptacle.

Clearly, the MICROCAM is truly a miniaturized version of the CAM sensor and of the concepts and teachings of the initial and instant applications.

While particular embodiments of the invention have been described, it will be apparent to those skilled in the art that various modifications thereof may be made without departing from the true spirit and scope of the invention. Accordingly, it is intended by the appended claims to cover all such modifications which embody the inventive features as defined in the claims.

TABLE 1

WEIGHING VOLUME POPULATION STATISTICS

| $\#/cm^3 > d_i$ $d_i$ in $\mu m$ | $\sigma_g = 0.5$ | $\sigma_g = 0.8$ | $\sigma_g = 1$ |
|---|---|---|---|
| $N_T$ | 60.66 | 18.68 | 6.34 |
| $N_1$ | 24.22 | 6.44 | 1.96 |
| $N_3$ | 0.43 | 0.72 | 0.35 |
| $N_5$ | 0.018 | 0.15 | 0.11 |
| $N_{10}$ | $7.048 \times 10^{-5}$ | 0.0093 | 0.017 |
| $N_{15}$ | 0 | 0.0026 | 0.0044 |
| $N_{20}$ | 0 | $4.39 \times 10^{-4}$ | 0.0017 |
| $N_{25}$ | 0 | $1.44 \times 10^{-4}$ | 0.0010 |
| $N_{30}$ | 0 | $3.92 \times 10^{-5}$ | 0.00073 |

Lognormal Distribution $$\rho(d) = \frac{1}{\sqrt{2\pi}\ \sigma_g d} e^{-\frac{(\ln d - \ln d_m)^2}{2\sigma_g^2}}$$

d = diameter
d̄ = number mean
$\sigma_g$ = geometrical standard deviation
$d_m$ = median diameter
Parameters
$\chi = 100\ \mu g/m^3$
$\rho = 1.5\ g/cm^3$
d̄ = 1 $\mu m$

We claim:

1. A method for providing in situ measurements of mass concentration of particulates entrained in ambient air comprising producing a beam of substantially monochromatic electromagnetic radiation, defining a sampling volume between the source of radiation and an optic receiver by the interception of said beam of radiation by the projected acceptance geometry of the optic receiver, directing said beam of radiation through said sampling volume for impingement upon a particle whose properties are to be measured, causing air to flow across the sampling volume by convection currents while restricting the flow of air through the sampling volume so as to cause a representative sample of said ambient air to be drawn across said sampling volume in a predetermined sampling interval of time having a duration such that no particle is sampled twice or more during the predetermined interval, collecting radiation from said sampling volume, and developing a signal related to the intensity of the collected radiation and processing said signal to obtain an output indicative of the mass concentration of the particulates passing through the sampling volume, and converting the signal into a read out signal corresponding to mass concentration of the particulates in the sampling volume.

2. A method as set forth in claim 1 wherein said convection currents are caused to occur by heating the representative sample of air.

3. A method as set forth in claim 1 wherein said step of drawing a sample of air includes restricting the flow of air across a predetermined cross sectional area defined in a plane normal to the direction of air flow and parallel to the beam.

4. A method as set forth in claim 1 wherein said step of drawing a representative sample of air includes simultaneously dessicating the sample of air.

5. A method as set forth in claim 1 wherein said beam of radiation has a diameter which is less than the product of the velocity of the sample of air drawn across the sampling volume and the predetermined sampling interval.

6. A method as set forth in claim 1 further including the step of establishing a process zero baseline for calibration of the measurement apparatus.

7. A method as set forth in claim 6 wherein said process zero is established by passing particle-free fluid through the sampling volume.

8. Electro-optical apparatus for providing in situ measurements of the mass concentration of particulates entrained in air comprising an electro-optical assembly including a source of substantially monochromatic electromagnetic radiation, optical means for directing a beam of said radiation through a sampling volume for impingement upon particulates contained therein whose mass concentration is to be measured, and receiver optics including photo detector means responsive to said radiation for developing an analog signal representative of radiation directed onto said detector means and indicative of the mass concentration of particulates in the sampling volume and optical means for collecting and directing radiation from said sampling volume traversed by said beam onto said photo detector, said sampling volume being defined by the interception of the beam of radiation by the projected acceptance geometry of the receiver optics, and a preseparator for drawing a representative sample of air across said sampling volume, said preseparator having an air flow channel open to the air at one end and a second end in communication with said sampling volume.

9. Apparatus as set forth in claim 8 wherein said preseparator is a vertical elutriator having said flow channel vertically disposed and said apparatus further includes a flow cell having a second cross channel normal to said first channel and in communication therewith, said optical assembly being disposed in said cross channel.

10. A system as set forth in claim 9 further including means collected to said detector means for classifying said analog signal according to whether small or large particulates are detected in the sampling volume and developing a classification signal in response thereto, means for subclassifying said classification signal according to the size thereof and developing an output in response thereto and means for operating on said output to develop a read out of the mass concentration of the particulates in the sampling volume.

11. Apparatus as set forth in claim 8 wherein said preseparator includes heater means for causing said air flow to occur through said preseparator by convection currents.

12. Apparatus as set forth in claim 8 including a flow cell disposed in said preseparator, said channel being defined at one end of said flow cell by an internal concave surface extending toward said sampling volume and terminating thereat in a restricted orifice.

13. A system as set forth in claim 8 further including means connected to said detector means for classifying said analog signal according to whether small or large particulates are detected in the sampling volume and developing a classification signal in response thereto, means for sub-classifying said classification signal according to the size thereof and developing an output in response thereto and means for operating on said output to develop a read out of the mass concentration of the particulates in the sampling volume.

14. A system as set forth in claim 13 wherein said preseparator for drawing air includes a flow cell arranged to restrict the flow of air to a predetermined region, said flow cell having a restricted opening of predetermined cross sectional area defined in a plane normal to the direction of air flow.

15. An electro-optical system for electro-optically weighing, in situ, particulates entrained in air comprising means for producing a beam of substantially monochromatic electromagnetic radiation, a sampling volume disposed between said means for producing said beam of radiation and receiver optics means having a radiation acceptance geometry and having a major axis along said beam, means for directing said beam of radiation through said sampling volume where it may impinge upon an object whose properties are to be measured, means for drawing a representative sample of ambient air containing the particulates to be weighed in a path crossing and normal to the major axis of the sampling volume in a predetermined interval of time having a duration such that no particle is sampled twice or more during the predetermined interval, said receiver optics means including detector means for developing an analog signal related to the intensity of radiation directed onto said detector means and optical means for collecting and focusing onto said detector means radiation scattered from said sampling volume traversed by said beam and periodically blocking said beam and redirecting a predetermined fraction of said beam onto said optical means and for periodically interrupting said scattered radiation such that said analog signal includes a plurality of time varying signal components including a calibration signal component, a zero signal component and a means connected to said detector for processing said analog signal to develop an output signal corresponding to the mass concentration of the particulates in the sampling volume.

16. A system as set forth in claim 15 wherein said means connected to said detector includes means for classifying said analog signal according to whether small or large particulates are detected in the sampling volume and developing a classification signal in response thereto, means for sub-classifying said classification signal according to the size thereof and developing an output signal in response thereto and means for operating on said output signal to develop a read out of the mass concentration of the particulates in the sampling volume.

17. A system as set forth in claims 15 or 16 wherein said means for drawing air includes a flow cell arranged to restrict the flow of air to a predetermined region having a restricted opening of predetermined cross sectional area defined in a plane normal to the direction of air flow.

18. An electro-optical system for electro-optically weighing, in situ, particulates entrained in ambient air comprising means for producing a beam of substantially monochromatic electromagnetic radiation, a sampling volume disposed between said means for producing said beam of radiation and receiver optics means having a radiation acceptance geometry whose projection intercepts said beam of radiation, said sampling volume being defined by the interception of said beam of radiation by said projected acceptance geometry and having a major axis along said beam, means for directing said beam of radiation through said sampling volume where it may impinge upon an object whose properties are to be measured, preseparator means for drawing a representative sample of ambient air containing the particulates to be weighed in a path crossing and normal to the major axis of the sampling volume, said receiver optics means including detector means for developing an analog signal related to the intensity of radiation directed onto said detector means and optical means for collecting and focusing onto said detector means radiation scattered from said sampling volume traversed by said beam and calibration/zero control means disposed between said sampling volume and the receiver optics means for periodically blocking said beam and redirecting a predetermined fraction of said beam onto said optical means and for periodically interrupting said scattered radiation such that said analog signal includes a plurality of time varying signal components including a calibration signal component, a zero signal component and a measurement signal component, means for processing said analog signal to develop individual control signals corresponding to said signal components for providing automatic compensation of the electro-optical system and means responsive to said analog signal for developing read out information corresponding to the mass concentration of the particulates in the sampling volume.

19. An electro-optical system for measurement of mass concentration of particulates in an open work area comprising a plurality of remote monitoring stations disposed at various locations in the work area, each location including a terminal box, means for connecting each said terminal box to an air source connected for air flow in both directions and for electrically connecting each said terminal box to a central control station, at least one electro-optical aerosol monitor supported adjacent a terminal box, means connecting said monitor through said terminal box to the air source and control station for operation thereof, each said monitor including a horizontally disposed electro-optical assembly and a vertically disposed preseparator having a central channel including a lower opening in communication with the open work area and an upper opening in communication with the air source through said terminal box, each said monitor comprising a source of substantially monochromatic electromagnetic radiation, optical means for directing a beam of said radiation through a sampling volume for impingement upon particulates contained therein whose mass concentration is to be measured, and receiver optics including photo detector means responsive to said radiation for developing an analog signal representative of radiation directed onto said detector means and indicative of the mass concentration of particulates in the sampling volume and optical means for collecting and directing radiation from said sampling volume traversed by said beam, said sampling volume being defined by the interception of the beam of radiation by the projected acceptance geometry of the optic receiver, and said channel of said preseparator being disposed along an axis intercepting said sample volume to allow a representative sample of air to flow across said sampling volume.

20. A system as set forth in claim 19 further including means connected to said photodetector means for classifying said analog signal according to whether small or large particulates are detected in the sampling volume and developed a classification signal in response thereto, means for sub-classifying said classification signal according to the size thereof and developing an output signal in response thereto and means for operating on said output signal to develop a read out of the mass concentration of the particulates in the sampling volume.

21. A system as set forth in claims 20 wherein said preseparator includes a flow cell arranged to restrict the flow of air to a predetermined region and having a restricted opening of predetermined cross sectional area defined in a plane normal to the direction of air flow.

22. A system as defined in claims 15, 16, 18 or 13, further including precipitator means for desiccating the sample of air as it flows through said separator.

23. A system as set forth in claim 22 wherein said precipitator means for desiccating comprises a heater within the separator.

24. A system as defined in claims 8 or 15, further including precipitator means for causing particle free fluid to pass through the sampling volume.

25. A system as defined in claims 8, 15, 18 or 19 further including calibration means adapted to be positioned directly in the sampling volume for calibration of the electro-optical apparatus and to be removed from the sampling volume when determining the mass concentration of particulates in the sampling volume.

26. A system as defined in claim 25 wherein said calibration means is rotatably supported for positioning within the sampling volume and in the path of the beam of radiation.

27. A system as defined in claim 25 wherein said calibration means includes a plurality of calibration elements each adapted to be positioned in the sampling volume.

28. A system as defined in claim 27 wherein said calibration means is rotatable about an axis disposed to the side of the axis of the beam.

29. A system as defined in claim 27 wherein said axis is normal to the axis of the beam.

30. A system as defined in claims 19 or 20 wherein said precipitator includes means for desiccating the sample of air as it flows through said separator.

31. A system as defined in claim 18 or 19 further including means connected to said pre-separator, for causing particle free fluid to pass through the sampling volume.

32. A portable electro-optical air monitor for providing in situ measurements of the mass concentration of particulates entrained in air and adapted to be externally worn by a worker in the area in which the air is to be monitored comprising a housing, an electro-optical assembly within said housing including a source of substantially monochromatic electromagnetic radiation, optical means for directing a beam of said radiation through a sampling volume for impingement upon particulates and scattering of radiation from said particulates contained therein whose mass concentration is to be measured, and receiver optics including photo detector means responsive to scattered radiation for developing a signal representative of scattered radiation directed onto said detector means and indicative of the mass concentration of particulates in the sampling volume and processing said signal to develop an output corresponding to the mass concentration of the particulates in the sampling volume and optical means for collecting and directing radiation from said sampling volume traversed by said beam onto said photodetector, said sampling volume being defined by the interception of the beam of radiation by the projected acceptance geometry of the receiver optics, and said housing having a plurality of apertures on opposite sides of said sampling volume for drawing a representative sample of air across said sampling volume.

33. A portable air monitor for providing in situ measurements of the mass concentration of particulates as set forth in claim 32 wherein said housing includes a removable cap at one end of said housing, a connector within said housing, said connector being accessible from exterior of said housing upon removal of said cap to allow excess to the data collected by said photodetector from an external source.

34. A monitor as set forth in claim 33 including a calibration element having a first stow position clear of the radiation beam and a second position in the path of said beam and in the sampling volume, and means for pivoting said element between the first and second positions.

35. A portable air monitor for electro-optically weighing, in situ, particulates entrained in air comprising a monitor housing adapted to be worn by a worker exposed to the air being monitored, said housing containing means for producing a beam of substantially monochromatic electromagnetic radiation, a sampling volume disposed between said means for producing said beam of radiation and receiver optic means having a radiation acceptance geometry whose projection intercepts said beam of radiation, said sampling volume being defined by the interception of said beam of radiation by said projected acceptance geometry and having a major axis along said beam, means within said housing for directing said beam of radiation through said sampling volume where it may impinge upon an object whose properties are to be measured, a plurality of openings on opposite sides of said housing and on opposite sides of the sampling volume for drawing ambient air containing the particulates to be weighed in a path crossing and normal to the major axis of the sampling volume, said receiver optics means including detector means for developing an analog signal related to the intensity of radiation directed onto said detector means and optical means for collecting and focusing onto said detector means radiation scattered from said sampling volume traversed by said beam and periodically blocking said beam and redirecting a predetermined fraction of said beam onto said optical means and for periodically interrupting said scattered radiation such that said analog signal includes a plurality of time varying signal components including a calibration signal component, a zero signal component and means connected to said detector for processing said analog signal to develop an output signal corresponding to the mass concentration of the particulates in the sampling volume.

36. A system as set forth in claim 35 wherein said means connected to said detector includes means for classifying said analog signal according to whether small or laarge particulates are detected in the sampling volume and developing a classification signal in response thereto, means for sub-classifying said classification signal according to the size thereof and developing an output signal in response thereto and means for operating on said output signal to develop a read out of the mass concentration of the particulates in the sampling volume.

37. A method for providing in situ measurements of mass concentration of particulates entrained in ambient air comprising producing a beam of substantially monochromatic electromagnetic radiation, defining a sampling volume between the source of radiation and an optic receiver by the interception of said beam of radiation by the projected acceptance geometry of the optic receiver, directing said beam of radiation through said sampling volume for impringement upon a particle or particles whose properties are to be measured, controlling and restricting the flow of air through the sampling volume so as to cause a representative sample of said ambient air to be drawn across said sampling volume by connection currents in a predetermined sampling interval of time having a duration such that no particle is sampled twice or more during the predetermined interval, collecting radiation from said sampling volume, and developing a signal related to the intensity of the collected radiation and processing said signal to obtain an output indicative of the mass concentration of the particulates passing through the sampling volume.

38. A method as set forth in claim 37 wherein said convection currents are caused to occur by heating the representative sample of air.

39. A method as set forth in claim 37 wherein said step of drawing a sample of air includes restricting the flow of air across a predetermined cross sectional area defined in a plane normal to the direction of air flow and parallel to the beam.

* * * * *

UNITED STATES PATENT AND TRADEMARK OFFICE
CERTIFICATE OF CORRECTION

PATENT NO. : 4,473,296

DATED : September 25, 1984

INVENTOR(S) : Frederick M. Shofner; Gerhard Kreikebaum; Arthur C. Miller, Jr.

It is certified that error appears in the above-identified patent and that said Letters Patent is hereby corrected as shown below:

In Claim 20, Line 18, delete "and developed a" and substitute -- and developing a --.

Signed and Sealed this

Twenty-sixth Day of March 1985

[SEAL]

*Attest:*

DONALD J. QUIGG

*Attesting Officer*     *Acting Commissioner of Patents and Trademarks*